(12) United States Patent
Jantzen et al.

(10) Patent No.: US 9,345,600 B2
(45) Date of Patent: *May 24, 2016

(54) GRADUALLY SELF-EXPANDING STENT

(71) Applicant: Cook Medical Technologies LLC, Bloomington, IN (US)

(72) Inventors: Alexandra E. Jantzen, Durham, NC (US); Nathaniel A. Irwin, Bloomington, IN (US); Jeffry S. Melsheimer, Springville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/302,872

(22) Filed: Jun. 12, 2014

(65) Prior Publication Data

US 2014/0296956 A1 Oct. 2, 2014

Related U.S. Application Data

(63) Continuation of application No. 12/342,302, filed on Dec. 23, 2008, now Pat. No. 8,764,813.

(51) Int. Cl.
| | |
|---|---|
| *A61F 2/06* | (2013.01) |
| *A61F 2/90* | (2013.01) |
| *A61F 2/07* | (2013.01) |
| *A61F 2/91* | (2013.01) |
| *A61F 2/915* | (2013.01) |
| *A61L 31/14* | (2006.01) |
| *A61L 31/16* | (2006.01) |
| *A61F 2/82* | (2013.01) |

(52) U.S. Cl.
CPC ... *A61F 2/90* (2013.01); *A61F 2/07* (2013.01); *A61F 2/91* (2013.01); *A61F 2/915* (2013.01); *A61L 31/148* (2013.01); *A61L 31/16* (2013.01); *A61F 2002/823* (2013.01); *A61F 2002/91558* (2013.01); *A61F 2210/0076* (2013.01); *A61F 2230/008* (2013.01); *A61F 2230/0078* (2013.01)

(58) Field of Classification Search
CPC .............. A61F 2/86; A61F 2250/0014; A61F 2250/003; A61F 2250/0031
USPC ........................................ 623/1.38, 1.3, 1.31
See application file for complete search history.

(56) References Cited

U.S. PATENT DOCUMENTS

| | | | |
|---|---|---|---|
| 5,195,984 | A | 3/1993 | Schatz |
| 5,236,447 | A | 8/1993 | Kubo et al. |
| 6,120,534 | A | 9/2000 | Ruiz |
| 6,146,416 | A | 11/2000 | Andersen et al. |
| 6,258,117 | B1 | 7/2001 | Camrud et al. |
| 6,312,461 | B1 | 11/2001 | Unsworth et al. |
| 6,334,868 | B1 | 1/2002 | Ham |
| 6,336,937 | B1 | 1/2002 | Vonesh et al. |
| 6,350,277 | B1 | 2/2002 | Kocur |
| 6,485,510 | B1 | 11/2002 | Camrud et al. |
| 6,613,077 | B2 | 9/2003 | Gilligan et al. |
| 6,652,576 | B1 | 11/2003 | Stalker |

(Continued)

*Primary Examiner* — Jacqueline Woznicki
(74) *Attorney, Agent, or Firm* — Brinks Gilson & Lione

(57) ABSTRACT

A gradually self-expanding stent is provided with a first region of stent cells. A restraining material is attached to the first region and restrains the first region from expanding to the expanded configuration. Over time the restraining material releases the first region to allow the first region to expand to the expanded diameter. The first region is located longitudinally between two second regions. The second regions expand at a faster rate than the first region.

21 Claims, 15 Drawing Sheets

(56) References Cited

U.S. PATENT DOCUMENTS

| | | |
|---|---|---|
| 6,663,664 B1 | 12/2003 | Pacetti |
| 6,699,280 B2 | 3/2004 | Camrud et al. |
| 7,011,678 B2 | 3/2006 | Tenerz et al. |
| 7,022,132 B2 | 4/2006 | Kocur |
| 8,252,043 B2 | 8/2012 | Case et al. |
| 2002/0143381 A1* | 10/2002 | Gilligan et al. ............... 623/1.2 |
| 2004/0230288 A1 | 11/2004 | Rosenthal |
| 2004/0260377 A1 | 12/2004 | Flomenblit et al. |
| 2005/0113904 A1 | 5/2005 | Shank et al. |
| 2006/0069424 A1* | 3/2006 | Acosta et al. ............... 623/1.12 |
| 2006/0259136 A1 | 11/2006 | Nguyen et al. |
| 2007/0142907 A1 | 6/2007 | Moaddeb et al. |
| 2007/0219626 A1 | 9/2007 | Rolando et al. |
| 2007/0254012 A1 | 11/2007 | Ludwig et al. |
| 2008/0082162 A1 | 4/2008 | Boismier et al. |
| 2009/0276036 A1 | 11/2009 | Nagura et al. |

\* cited by examiner

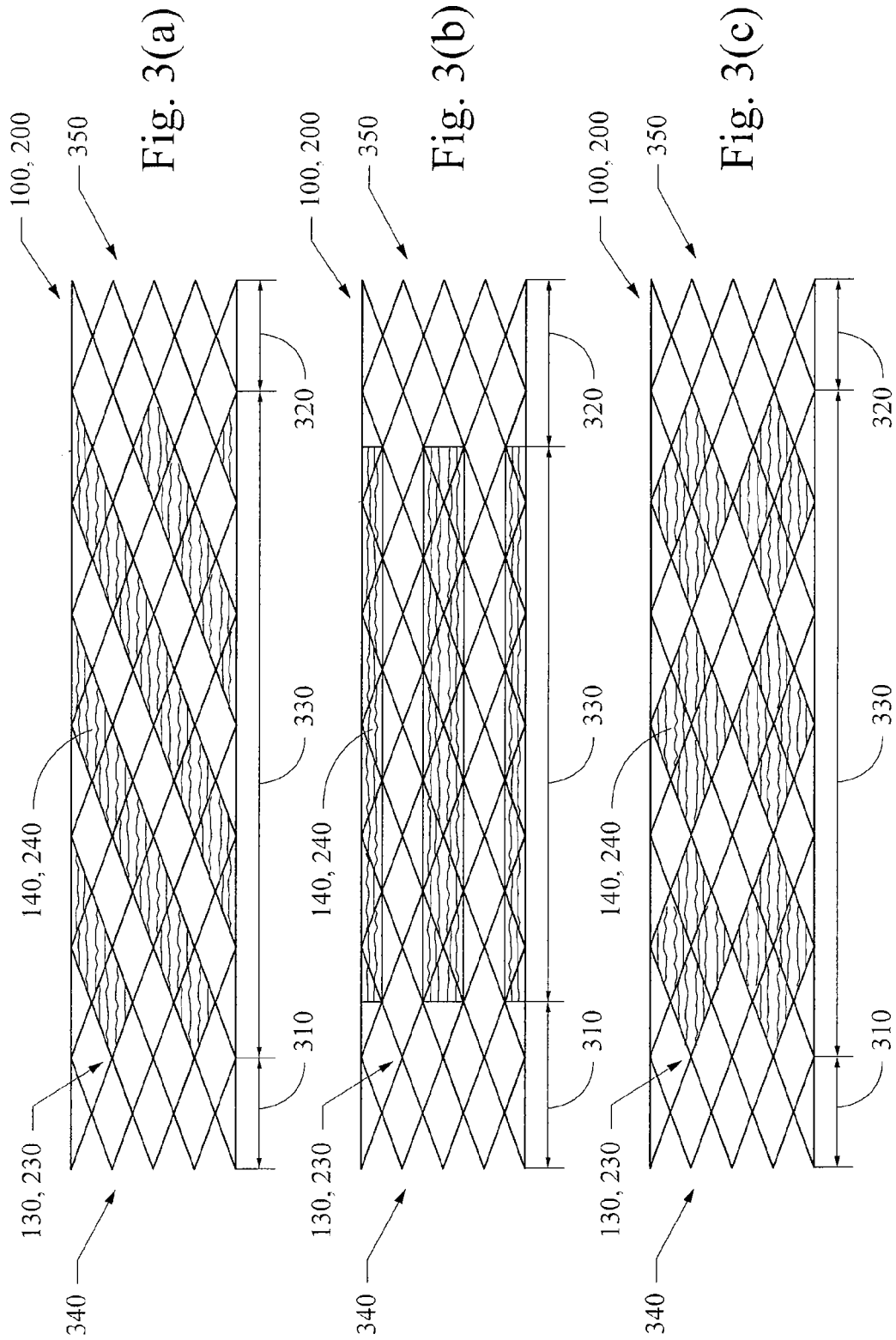

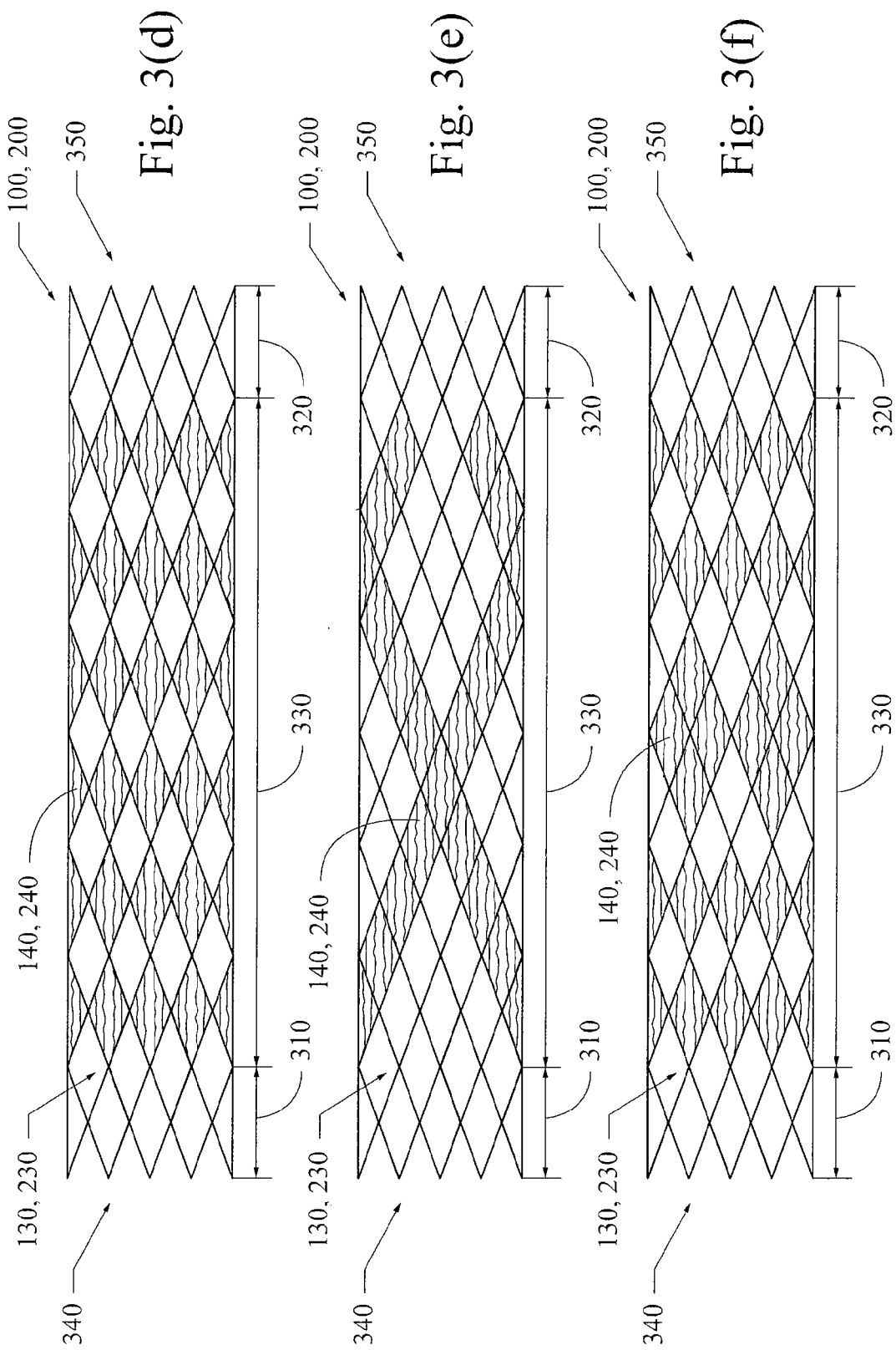

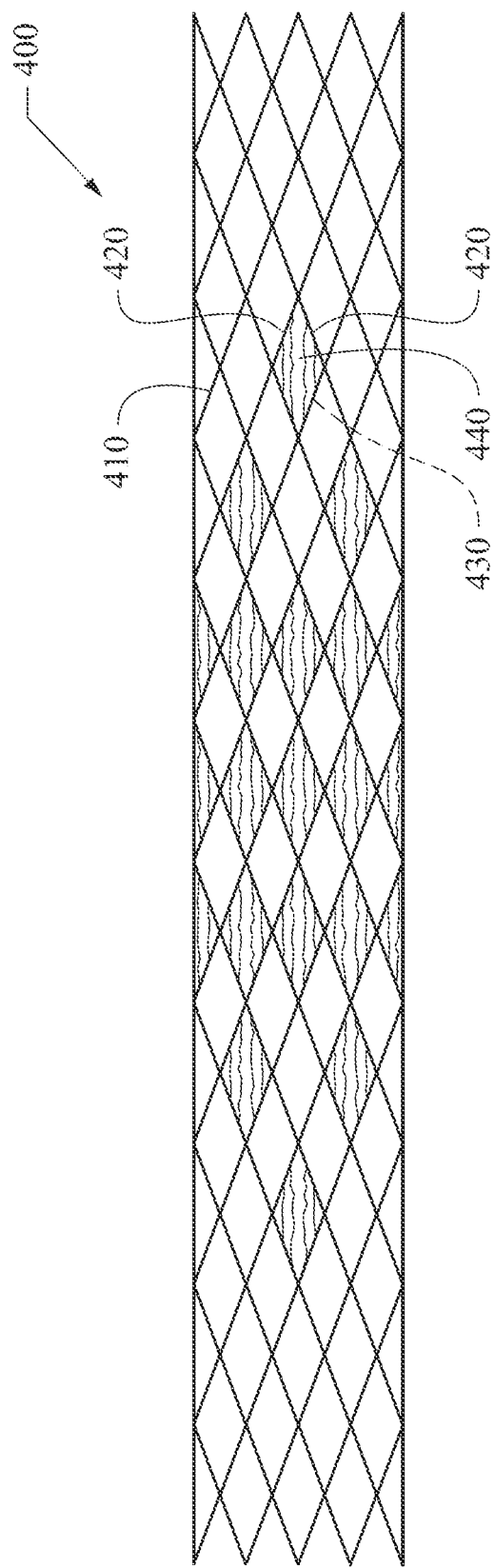

GRADUALLY SELF-EXPANDING STENT

This application is a continuation of U.S. patent application Ser. No. 12/342,302, filed Dec. 23, 2008, which is incorporated herein by reference in its entirety.

BACKGROUND

The present invention relates generally to medical devices and more particularly to self-expanding stents.

Stents have become a common alternative for treating vascular conditions because stenting procedures are considerably less invasive than other alternatives. As an example, stenoses in the coronary arteries have traditionally been treated with bypass surgery. In general, bypass surgery involves splitting the chest bone to open the chest cavity and grafting a replacement vessel onto the heart to bypass the stenosed artery. However, coronary bypass surgery is a very invasive procedure that presents increased risk and requires a long recovery time for the patient. By contrast, stenting procedures are performed transluminally and do not require open surgery. Thus, recovery time is reduced and the risks of surgery are minimized.

Many different types of stents and stenting procedures are possible. In general, however, stents are typically designed as tubular support structures that may be inserted percutaneously and transluminally through a body passageway. Typically, stents are adapted to be compressed and expanded between a smaller and larger diameter. However, other types of stents are designed to have a fixed diameter and are not generally compressible. Although stents may be made from many types of materials, including non-metallic materials and natural tissues, common examples of metallic materials that may be used to make stents include stainless steel and nitinol. Other materials may also be used, such as cobalt-chrome alloys, amorphous metals, tantalum, platinum, gold, titanium, polymers and/or compatible tissues. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through narrow, tortuous passageways to the area to be treated while the stent is in a relatively small, compressed diameter. Once the stent has been positioned and expanded at the area to be treated, the tubular support structure of the stent contacts and radially supports the inner wall of the passageway. The implanted stent may be used to mechanically prevent the passageway from closing in order to keep the passageway open to facilitate fluid flow through the passageway.

One common type of stent used in medical procedures is the self-expanding stent. Self-expanding stents are usually made of shape memory materials or other elastic materials that act like a spring. Self-expanding stents are increasingly being used by physicians because of their adaptability to a variety of different conditions and procedures. Typical metals used in this type of stent include nitinol and stainless steel. However, other materials may also be used. To facilitate stent implantation, self-expanding stents are normally installed on the end of a delivery catheter in a low profile, compressed state. The stent is typically inserted into a sheath at the end of the catheter, which restrains the stent in the compressed state. The stent and catheter assembly is then guided along a guide wire to the portion of the vessel to be treated using the Seldinger technique, which is well known in the art. Once the catheter and stent are positioned adjacent the portion of the vessel to be treated, the stent is released by pulling, or withdrawing, the sheath rearward. Normally, a stop or other feature is provided on the catheter to prevent the stent from moving rearward with the sheath. After the stent is released from the retaining sheath, the stent springs radially outward to an expanded diameter until the stent contacts and presses against the vessel wall. Generally, self-expanding stents are selected such that the expanded outer diameter of the stent is greater than the inner diameter of the blood vessel. In this way, the continuous outward force of the stent against the inner surface of the blood vessel helps to hold the stent in the deployment location and prevent migration of the stent through the vessel.

Traditionally, self-expanding stents have been used in a number of peripheral arteries in the vascular system due to the elastic characteristic of these stents. However, they may be used in the coronary, carotid, femoral, and renal arteries as well. One advantage of self-expanding stents for peripheral arteries is that stresses from external sources do not permanently deform the stent. As a result, the stent may temporarily deform during unusually harsh stresses and spring back to its expanded state once the stress is relieved. However, self-expanding stents may be used in many other currently known or later developed applications as well.

Self-expanding stents are commonly used in angioplasty, or the mechanical widening of narrowed or completely obstructed blood vessels. Typically, the blood vessels are narrowed or obstructed as a result of arteriolosclerosis or atherosclerosis. Angioplasty is generally performed using a balloon that is tightly folded around a catheter. The catheter is delivered to the treatment site using the aforementioned Seldinger technique, and the balloon is inflated with a fluid, typically saline, contrast, or a mixture thereof. The fluid is injected into the balloon using pressures that are much higher than normal blood pressures until the balloon is inflated to a fixed, predetermined size. This high pressure inflation of the balloon forces the vessel wall at the treatment site to expand in a radially outward direction, thereby widening the obstructed portion of the blood vessel.

Once the blood vessel has been expanded, a self-expanding stent is delivered to the treatment site and deployed into the blood vessel in the above described manner. Because the self-expanding stent acts like a spring, once the stent is released from the delivery catheter it immediately expands to the inner diameter of the blood vessel and continuously exerts outward pressure against the vessel wall. While this outward pressure helps to maintain the position of the stent, the sudden application of outward pressure by the stent against the wall of a vessel that has just undergone balloon expansion may further traumatize the vessel tissue. Such trauma may give rise to potential problems such as hyperplasia, or the abnormal proliferation of cells at the treatment site.

Current research has shown that hyperplastic response to angioplasty or stenting appears to be greatly increased in vessels where the internal elastic lamina ("IEL") layer of the vessel is ruptured during the angioplasty or stenting procedure. In areas where the IEL is ruptured or damaged, the blood vessel usually exhibits a healing inflammatory response in the form of neointimal growth (abnormal increased growth of cells), which may lead to restenosis, or re-narrowing of the blood vessel. In contrast, areas of the blood vessel where the IEL is left intact tend not to exhibit such neointimal growth. Consequently, it is preferable to leave the IEL intact during the stenting procedure in order to reduce hyperplasia/neointimal growth.

One attempt to reduce stent caused trauma to blood vessel tissue is illustrated by U.S. Pat. No. 6,613,077 to Gilligan et al. Gilligan et al. proposes the use of biodegradable sutures circumferentially wound tightly around the exterior of a stent. After the stent is deployed in a vessel, the constraining sutures restrain the stent from fully expanding. As the sutures begin to biodegrade they yield and then break, thereby releasing the stent against the vessel wall. However, because the sutures are wrapped around the circumference of the stent, once the suture fails, the entire circumference of the stent immediately and suddenly expands to contact the vessel wall.

Similarly, U.S. Pat. No. 7,022,132 to Kocur proposes biodegradable bands that are wrapped around the exterior of the stent or interwoven around the circumference of the stent. Kocur also proposes biodegradable bands wrapped around two individual stent struts. In each case, the bands are designed to initially hold the stent in a compressed shape. As the bands biodegrade they fracture, thereby immediately and suddenly releasing the stent against the vessel wall.

However, these techniques may unnecessarily traumatize the IEL by suddenly expanding against the vessel wall when the sutures or bands fail. Further, these techniques present significant manufacturing obstacles as the sutures and bands must be wound, woven, and/or tied around the circumference of the stent or individual stent struts to keep the stent or portions thereof in a compressed configuration. It has become apparent to the inventor that an improved stent would be desirable.

SUMMARY

Self-expanding stents are described which may allow for more gentle and gradual expansion against a vessel wall. The gradually self-expanding stent includes a restraining material that covers and restrains at least some stent cells in a compressed configuration after deployment in a body lumen. Additional details and advantages are described below in the detailed description.

The invention may include any of the following aspects in various combinations and may also include any other aspect described below in the written description or in the attached drawings.

In one aspect, a gradually self-expanding stent includes a stent structure formed from a series of structural members that are designed to flex between expanded and compressed configurations. The stent structure has a generally cylindrical shape in its uncompressed configuration. The self-expanding stent also includes a first plurality of stent cells, each stent cell having an area defined by circumferentially adjacent structural members that are in mechanical communication with one another. When the circumferentially adjacent structural members of the stent cells are in the compressed configuration, the stent cells have a first area. When the structural members of the stent cells are in the expanded configuration, the stent cells have a second area that is larger than the first area.

A restraining material substantially covers the area of a second plurality of stent cells. The restraining material preferably restrains each of the plurality of stent cells in the compressed configuration. The restraining material may be attached to the circumferentially adjacent structural members defining each stent cell in the second plurality of stent cells. Over time, the restraining material is configured to release the structural members defining the stent cells, thereby allowing the stent cell to assume its expanded configuration.

In one aspect, the restraining material may be biodegradable. In another aspect, the restraining material may be stretchable. In yet another aspect, the restraining material may not extend around the circumference of the stent structure in a continuous manner.

In another embodiment, the gradually self-expanding stent may include a stent structure having a proximal end portion, a distal end portion, and a central portion. The proximal end portion may extend toward a longitudinal center of the stent structure from a proximal end thereof by an amount based on an overall length of the stent structure, while the distal end portion may extend toward the longitudinal center of the stent structure from a distal end thereof by an amount based on an overall length of the stent structure. The central portion is disposed between the proximal and distal end portions. Preferably, the stent cells of the proximal and distal end portions are comprised of the first plurality of stent cells, while the stent cells of the central portion are comprised of both the first and second plurality of stent cells.

In one aspect, a proportion of the first plurality of stent cells to the second plurality of stent cells in the central portion is substantially equal. The central portion may also include an intermediate portion, wherein the restraining material covering stent cells disposed in the intermediate portion is configured to release the structural members more quickly than the restraining material for stent cells disposed outside of the intermediate portion. The intermediate portion may include a proximal intermediate portion and a distal intermediate portion. The proximal intermediate portion preferably extends toward the longitudinal center of the stent structure from a distal end of the proximal end portion by a predetermined amount, while the distal intermediate portion extends toward the longitudinal center of the stent structure from a proximal end of the distal end portion by the predetermined amount. The predetermined amount is preferably based on a length of the central portion.

In another aspect, the restraining material of stent cells disposed in the intermediate portion may be configured to release the structural members more quickly than the restraining material of stent cells disposed outside of the intermediate portion.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

The invention may be more fully understood by reading the following description in conjunction with the drawings, in which:

FIG. 2(*a*) is a close-up side view of a plurality of stent cells of the embodiment of FIG. 2 showing an alternative configuration of a restraining material;

FIGS. 3(*a*)-(*f*) are side views of various embodiments of the self-expanding stent of FIG. 1 in a compressed state;

FIG. 4 is a side view of an embodiment of a self-expanding stent in a compressed state before deployment in a body lumen;

DETAILED DESCRIPTION

Figure 1:
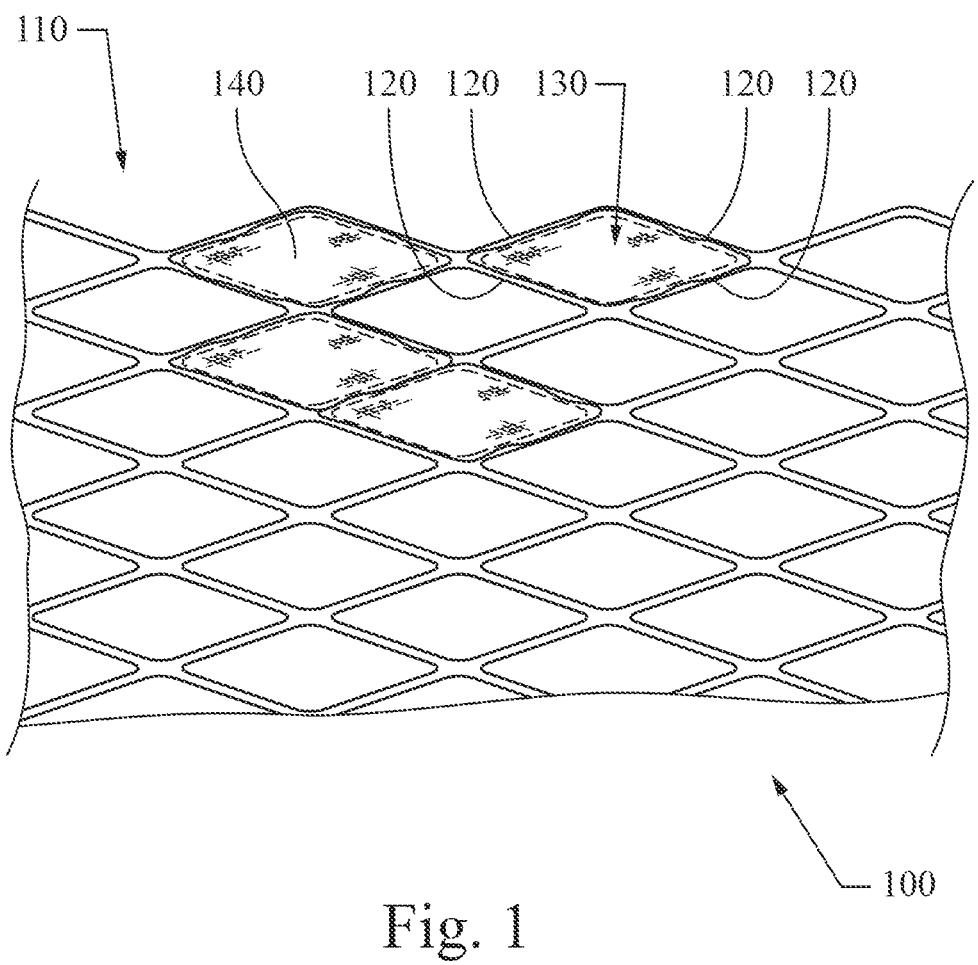
FIG. 1 is a close-up side view of a plurality of stent cells of a self-expanding stent in a compressed state.
Figure 2:
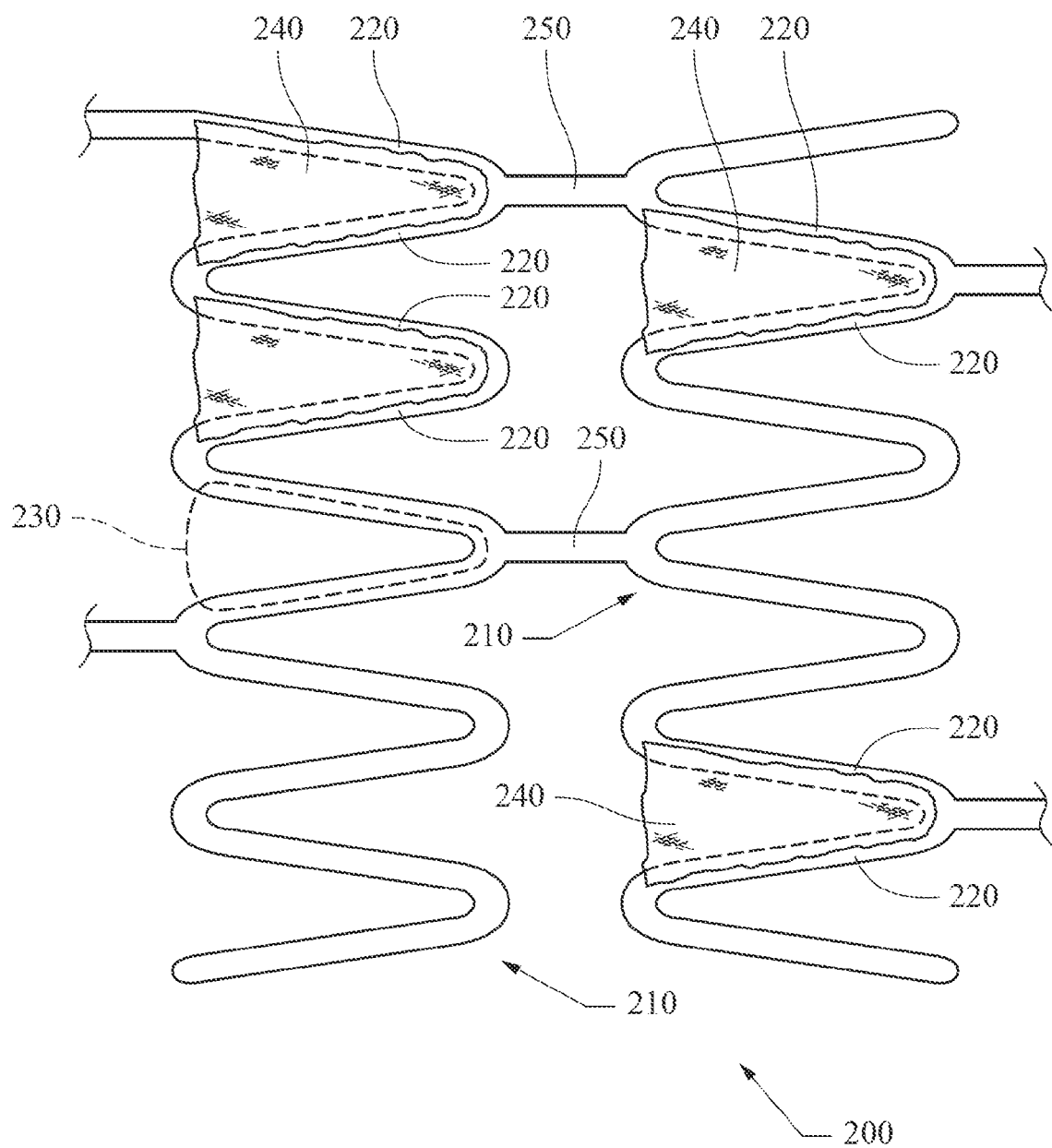
FIG. 2 is a close-up side view of a plurality of stent cells of an alternative embodiment of the self-expanding stent of FIG. 1 in a compressed state.

Referring now to the figures, FIGS. 1-3 illustrate a gradually self-expanding stent according to an embodiment of the present invention. The gradually self-expanding stent structure 100, 200 is particularly useful in lesions or areas where the narrowed or completely obstructed blood vessels are chronic rather than acute such that a gradual opening of the vessel would be clinically acceptable, for example and without limitation, peripheral arteries. Various designs known in the art may be used for the stent structure 100, 200. For example, the stent structure 100, 200 may be made with serpentine rings interconnected with longitudinal structural members. The stent structure 100, 200 may be fabricated from a cannula, and may have longitudinal segments of laterally interconnected closed cells, as disclosed in U.S. Pat. Nos. 6,231,598, and 6,743,252 which are assigned to Cook Inc., the assignee of the present invention and are hereby incorporated by reference in their entirety. Each of the closed cells may be at least partially defined laterally by a pair of longitudinal struts that are interconnected at each end by a circumferentially adjustable member. Each of the pair of longitudinal struts deforms or flexes to permit circumferential expansion while the length of the cell is maintained by the longitudinal struts. The stent may include adjacent longitudinal segments that are joined by flexible interconnection segments thereby permitting the stent to bend laterally and that are comprised of curvilinear struts that form a series of serpentine bends. The curvilinear struts may distribute lateral bending forces while only allowing a slight overall shortening of the stent structure 100, 200.

Alternatively, the stent structure 100, 200 may be a wire frame constructed from a plurality of wire stent segments as disclosed in U.S. Pat. No. 5,195,984. The stent structure 100, 200 may also be made from a braided framework of wire filaments. Other well-known stent structures are also possible. Various materials may be used for the self-expanding stent structure 100, such as nitinol or stainless steel.

FIG. 1 illustrates embodiments of the stent structure 100. The stent structure 100 is comprised of a plurality of interconnected structural members 110 that define a plurality of stent cells 130. Specifically, each stent cell 130 is defined by circumferentially adjacent structural members 120. As shown in FIG. 1, a pair of upper and lower structural members 120 may be connected to each other through apexes or transitional portions, or may be directly connected to each other. Each stent cell 130 has an area that is defined by the individual structural members 120 of each stent cell 130. Thus, in the embodiment shown in FIG. 1, each stent cell 130 has a shape and area resembling a parallelogram. However, it should be understood that the shape and corresponding area of the stent cells 130 are not limited thereto since the stent cell's 130 shape and area will substantially correspond to the geometric relationship between the circumferentially adjacent structural members 120.

The structural members 120 of each stent cell 130 are configured to flex between a compressed configuration and an expanded configuration. When the stent cells 130 are in the compressed configuration, the upper and lower pairs of circumferentially adjacent structural members 120 form an acute angle with one another such that an area of the stent cell 130 is minimized. In contrast, when the stent cells 130 are in the expanded configuration, the upper and lower pairs of circumferentially adjacent structural members 120 form a less acute, or even a right or obtuse angle between one another such that the area of the stent cell 130 is maximized. Note that the compressed configuration need not correspond to a maximally compressed configuration, and may refer to any intermediate configuration between the maximum compressed and expanded states, provided that the outer diameter of the stent structure 100 is smaller in the compressed configuration than in the expanded configuration. Similarly, the expanded configuration need not correspond to a maximally expanded configuration and may refer to any intermediate configuration between the maximum expanded and compressed states, provided that the outer diameter of the stent structure 100 is larger in the expanded configuration than in the compressed configuration.

Preferably, the structural members 110 of the stent structure 100 are made from elastic, super-elastic, or spring-metal alloys such as nitinol, stainless steel, cobalt chromium, nickel titanium, platinum, inconel, or any other material known in the art, such that the structural members 110 can compress under force, and when unrestrained will tend to return to the expanded configuration in a spring-like manner. Note that adjacent stent cells 130 may share some of the same structural members 120. That is, each of the structural members 110 may define two separate stent cells 130, one on each side of the structural member 110.

A restraining material 140 may be applied to some, but preferably not all of the stent cells 130 in the compressed configuration. Preferably, the restraining material is attached to each of the circumferentially adjacent structural members 120 and extends across the entirety of the area of the stent cell 130, thereby connecting the circumferentially adjacent structural members 120 to one another and restraining the structural members 120 in the compressed configuration. Because the restraining material 140 is attached to, and extends between each of the structural members 120, the restraining material 140 creates a restraining structure that holds the circumferentially adjacent structural members 120 of the stent cell 130 in the compressed configuration. Thus, the restraining material 140 prevents the structural members 120 from assuming the expanded configuration, even when the stent structure is no longer exposed to restraining or constraining forces in a radially inward direction.

Figure 2A:
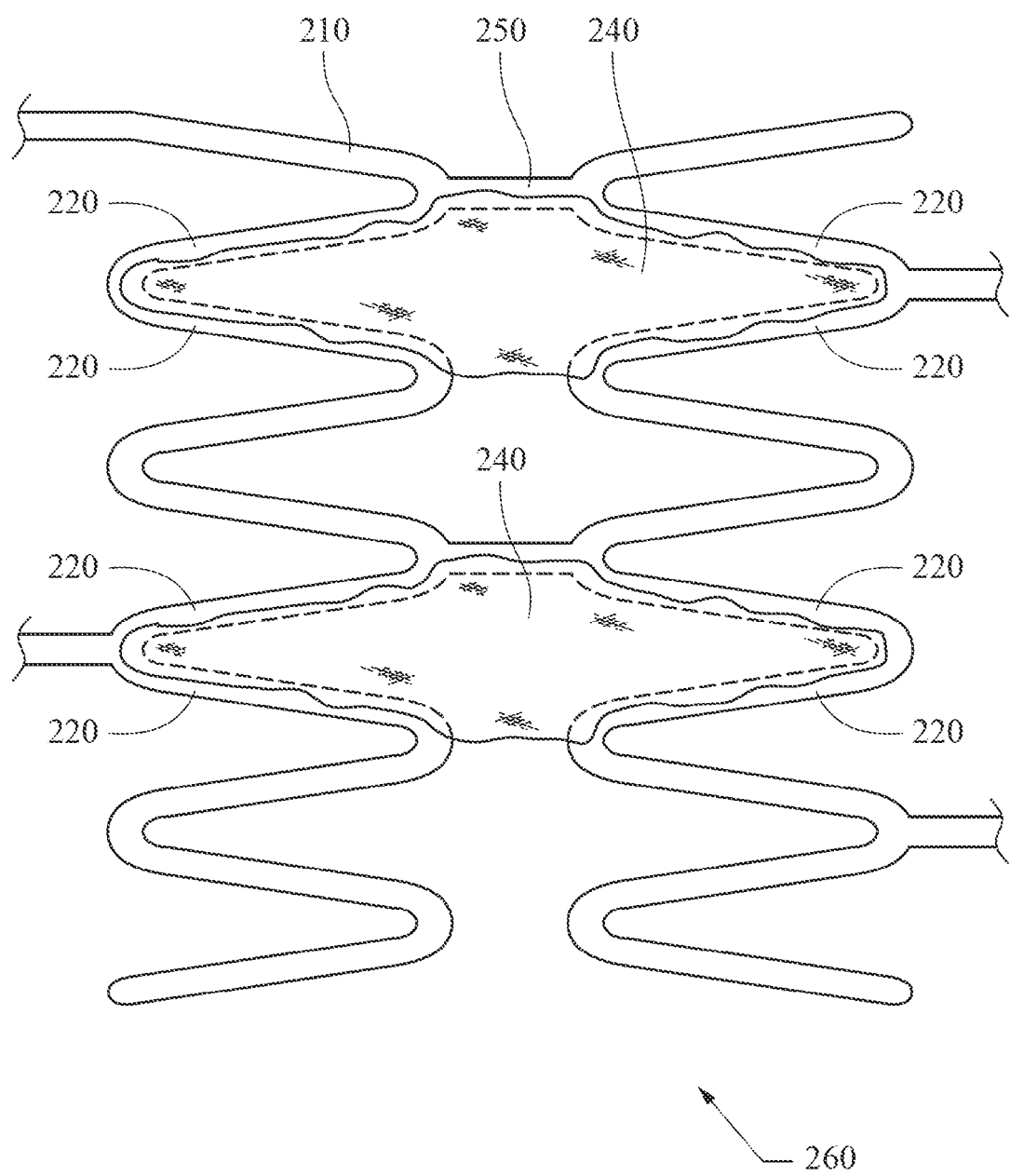

Turning to FIGS. 2 and 2(a), a stent structure 200 is comprised of a plurality of ring structures 260 connected by connecting members 250. Each of the stent rings 260 is comprised of a plurality of structural members 210 that are connected by apexes or connecting portions such that the structural members 210 form an undulating or serpentine structure. As with the stent structure 100 of FIG. 1, the structural members 210 define a plurality of stent cells 230. Specifically, each stent cell 230 is at least partially defined by circumferentially adjacent structural members 220. The circumferentially adjacent structural members 220 may be directly connected to one another, or may be connected via an apex or connecting portion such that the circumferentially adjacent structural members 220 are in mechanical communication with each other. In this configuration, each of the upper and lower circumferentially adjacent structural members 220 defines at least a portion of the cell 230. A pair of upper and lower structural members 220, which may be directly connected or connected through apexes or transitional portions, define at least a portion of the edge(s) of an area of a stent cell 230.

As with the stent structure 100 of FIG. 1, the structural members 210 are configured to flex between a compressed configuration and an expanded configuration. Thus, when the stent structure 200 is in the compressed configuration, the upper and lower pairs of circumferentially adjacent structural members 220 are disposed substantially adjacent to and abutting one another such that an area of the stent cell 130 is minimized. In contrast, when the circumferentially adjacent structural members 220 are in the expanded configuration, the upper and lower structural members 220 are angled away from each another such that the area of the stent cell 230 is maximized. As with the stent structure 100 of FIG. 1, it should be understood that the term compressed configuration need not correspond to a completely compressed configuration where the circumferentially adjacent structural members 220 abut each other. Thus the compressed configuration may refer to any intermediate configuration between the maximally compressed and expanded states, provided that the outer diameter of the stent structure 200 is smaller in the compressed configuration than in the expanded configuration. Similarly, the term expanded configuration need not correspond to a maximally expanded configuration and may refer to any intermediate configuration between the maximally expanded and compressed states, provided that the outer diameter of the stent structure 200 is larger in the expanded configuration than in the compressed configuration.

A restraining material 240 may be applied to some, but preferably not all of the stent cells 230 in the compressed configuration. Preferably the restraining material is attached to at least each of the circumferentially adjacent structural members 220 and extends at least across the space between the structural members 220. Because the restraining material 240 is attached to, and extends between each of the structural members 220, the restraining material 240 creates a restraining structure that holds the circumferentially adjacent structural members 220 of the stent cell 230 in the compressed configuration. Thus, the restraining material 240 prevents the structural members 220 from assuming the expanded configuration, even when the stent structure is no longer exposed to compressive forces.

As discussed above, the stent cell area is at least partially defined by the circumferentially adjacent structural members 220. In the embodiment shown in FIG. 2, the area of the stent cell 230 is defined primarily by the two circumferentially adjacent structural members 220, and the restraining material 240 extends therebetween. Preferably, the restraining material 240 is attached to the circumferentially adjacent structural members 220 and extends across the entirety of the area of the stent cell 230, as shown in FIG. 2.

FIG. 2(a) illustrates another embodiment in which the area of the stent cell is defined by two pairs of circumferentially adjacent structural members 220, each pair disposed on an adjacent ring structure 260. The two pairs of circumferentially adjacent structural members 220 may have a mirrored configuration in the longitudinal direction, as shown in FIG. 2(a), or may have the same longitudinal configuration. The restraining material is preferably attached to at least the structural members 220 of the stent cell 230. The restraining material 240 may extend across the entirety of the area of the stent cell 230, thereby connecting the circumferentially adjacent structural members 220 of each ring structure 260 to one another, as well as connecting the adjacent ring structures 260. Accordingly, the restraining material 240 acts to restrain the structural members 220 of the stent cells 230 from expanding after deployment in a body lumen, while simultaneously restraining relative movement between the adjacent ring structures 260.

The restraining material 140, 240 may be rigid or may be stretchable (e.g. capable of stretching or yielding through elastic or plastic deformation, or a combination thereof). Where the restraining material is stretchable, the restraining material may be made of biodegradable materials, nonbiodegradable materials, or a combination thereof. For example, a nonbiodegradable restraining material 140, 240 having stretchable characteristics may include elastic impregnated ePTFE.

Preferably, the restraining material is made from a biodegradable or bioabsorbable material that is configured to degrade or dissolve over time when exposed to body tissue and/or fluids. The restraining material may be made from one or more biodegradable polymers in varying combinations, such as polymers, copolymers, and block polymers. Some examples of such biodegradable (i.e. bio-resorbable/bioabsorbable) polymers include poly-lactic acid, polyglycolic acid, polyglycolides, polylactides, co-polymers of polyglycolides and polylactides, polycaprolactones, polyglycerol sebacate, polycarbonates (e.g. tyrosine derived polyethylene oxide), polybutylene terepthalate, polydioxanones, hybrids, composites, collagen matrices with growth modulators, polyanhydrides, polyorthoesters, chitosan, aliginates, proteoglycans, glycosaminoglycans, vacuum formed SIS (small intestinal submucosa), fibers, chitin, and dextran. Any of these biodegradable polymers may be used alone or in combination with these or other biodegradable polymers in varying compositions. Examples of biodegradable materials exhibiting rigid characteristics include chitosan, alginates, and co-polymers of polyglycolides and polylactides. Examples of biodegradable materials exhibiting stretchable characteristics include co-polymers of polycaprolactone with polyethylene, polypropylene, polyamids, or polyester.

In the case of rigid biodegradable restraining materials 140, 240, as the material degrades or dissolves, the radially outward force exerted by the structural members 110, 120 will eventually cause the restraining material 140, 240 to fracture when the force of the stent exceeds the ultimate tensile strength of the restraining material 140, 240. In the event the restraining material 140, 240 fractures such that one or more of the circumferentially adjacent structural members 120 is no longer connected to the other structural members 120, the disconnected structural member 120 is no longer restrained, and the energy stored within the structural member is released as the structural member 120 assumes its expanded configuration. Once the restraining material 140, 240 dissolves or fractures to the point that all of the circumferentially adjacent structural members 120 become disconnected from one another, the energy stored in each of the structural members 120 is released, and the stent cell 130, 230 assumes its expanded configuration.

In the case where the restraining material 140, 240 is a stretchable material, the stent cells 130, 230 achieve the expanded configuration through plastic or elastic deformation rather than through failure of the restraining material 140, 240. As with the rigid restraining material 140, 240, the stretchable restraining material 140, 240 is continually subjected to radially outward expansive force from the circumferentially adjacent structural members 120. The restraining material 140, 240 is configured to hold its initial shape during and shortly after deployment in a body lumen. However, over time, the outward force exerted by the structural members 120 causes the stretchable material to elongate or stretch in a gradual and controlled manner, thereby allowing the area of the attached stent cell 130, 230 to increase. The stretchable restraining material 140, 240 may be a nonbiodegradable material that is configured to stretch over time solely due to the elastic properties of the material, or the restraining material may be a biodegradable material that is configured to stretch as the restraining material 140, 240 degrades. However, it should be understood that the stretchable restraining material 140, 240 may stretch over time due to both the elastic properties of the material and the degradation of the material. Furthermore, it should be understood that the stent cells 130, 230 may expand through a combination of stretching and fracturing of the restraining material 140, 240. In this case, the restraining material 140, 240 may expand through stretching in one expansion stage and through fracture during another expansion stage.

As the area of the stent cells 130, 230 increase in size due to either the stretching or fracture of the restraining material 140, 240, the stent structure 100, 200 slowly expands from the compressed configuration, in which the portions of the stent structure 100, 200 containing stent cells 130, 230 covered by the restraining material 140, 240 do not abut the inner surface of a wall of the body lumen, to the expanded configuration where exterior surface of the stent structure 100, 200 abuts and engages the wall of the body lumen.

FIGS. 3(*a*)-(*f*) illustrate a plurality of exemplary patterns in which the restraining material 140, 240 may be applied to the stent cells 130, 230. Typically, the expanded, unrestrained diameter of the stent is selected by physicians such that the stent will appose the wall of the constricted vessel in its fully expanded form, while not migrating downstream. The length of the stent structure 100, 200 is generally specified such that it will cover the entirety of a lesion or narrowed/obstructed portion of the blood vessel and extend from healthy tissue to healthy tissue disposed on opposite ends thereof.

The stent structure 100, 200 may be divided into three expansion sections: a proximal end portion 310 that extends from the proximal end 340 of the stent structure 100, 200 to the proximal end of a central portion; the central portion 330 that extends from the distal end of the proximal end portion 310 to the proximal end of the distal end portion 320; and the distal end portion 320 that extends from the distal end of the central portion to the distal end 350 of the stent structure 100, 200. In order to ensure the stent structure 100, 200 is firmly fixed against healthy tissue at one or both ends of the stent structure 100, 200, it is preferable that the restraining material 140, 240 is not applied to the stent cells 130, 230 of the proximal and distal ends 310, 320 of the stent structure 100, 200. In this way, when the stent structure is deployed in a body lumen, the proximal and distal ends 310, 320 of the stent structure 100, 200 are free to fully and immediately expand outward to appose the healthy tissue of the body lumen, thereby fixing the stent in place.

The proximal and distal end portions 310, 320 of the stent structure 100, 200 preferably have sufficient length to allow the struts 120, 220 to expand out and appose the healthy tissue of the body lumen (blood vessel, etc.) with sufficient force to maintain the position of the stent structure 100, 200. For example, for stents having a length of less than thirty (30) millimeters the proximal end portion 310 and the distal end portion 320 may have a length of five (5) millimeters or less. Stent structures having a length of greater than thirty (30) millimeters (e.g. 50 mm, 100 mm, 140 mm, etc.) may have proximal and distal end portions 310, 320 measuring less than or equal to ten (10) millimeters.

As shown in FIGS. 3(*a*)-(*f*), the majority of stent cells 130, 230 covered by the restraining material 140, 240 are preferably located in the central portion 330 of the stent structure 100, 200. In this way, when the stent structure 100, 200 is deployed in a blood vessel, the ends of the stent structure are able to immediately expand out and appose the vessel wall, while the central portion 330 of the stent structure 100, 200 remains substantially in the compressed configuration due to the restraining material 140, 240. Preferably, the pattern of restrained stent cells 130, 230 does not extend in a continuous manner around the entire circumference of the stent structure at any given longitudinal position along the stent structure 100, 200. Thus, the restraining material does not form a continuous circumferential band of restraining material at any given longitudinal position along the length of the stent structure 100, 200. In this way, when a single or a group of stent cells 130, 230 expands through stretching or fracturing of the restraining material 140, 240, the expansion of the stent structure 100, 200 is limited to that portion of the stent. Because the expansion of the stent structure 100, 200 is localized, the entire circumference of the stent structure 100, 200 is less likely to suddenly or immediately expand and apply significant force to the tissue of the lesion/stricture, thereby minimizing the potential of rupturing the IEL.

Preferably, the restraining material 140, 240 is only applied to a plurality of stent cells 130, 230 disposed in the central portion 330 of the stent structure 100, 200. In this way, the proximal and distal end portions of the stent structure 100, 200, which contain only open cells 130, 230, are allowed to expand out to the inner diameter of the body lumen (e.g. blood vessel, etc.) upon deployment, while the central portion 330 remains partially restrained such that the overall profile of the stent structure 100, 200 assumes an hourglass-like shape.

As shown in FIGS. 3(*a*)-(*f*), the restraining material 140, 240 is preferably applied in a substantially uniform manner such that roughly 50% of the total number of stent cells 130, 230 in the central portion 330 are covered by the restraining material 140, 240. However, it should be understood that the present invention is not limited thereto, and the restraining material 140, 240 may be applied to more or less than 50% of the stent cells 130, 230 of the central portion 330 in order to adjust the degree of initial expansion of the stent structure 100, 200 upon deployment. In particular, embodiments having 25-30% of the stent cells 130, 230 disposed in the central portion 330 restrained by the restraining material 140, 240 for less restrained configurations, and embodiments having 50-75% of the stent cells 130, 230 disposed in the central portion 330 restrained by the restraining material 140, 240 for more restrained configurations are contemplated.

Because some of the stent cells 130, 230 in the central portion 330 are unrestrained by the restraining material 140, 240, the unrestrained cells 130, 230 are free to assume their fully expanded configuration when the stent structure 100, 200 is deployed (released) in a body lumen. However, because some of the stent cells 130, 230 are restrained in their compressed configuration by the restraining material 140, 240, the overall diameter of the central portion 330 of the stent structure 100, 200 is initially only able to expand partially upon deployment. Preferably, the stent structure 100, 200 is only able to expand to 30% to 50% of its unrestrained diameter in an initial state after deployment. Preferably, the degree of initial expansion is selected based on the characteristics of the stricture/lesion the stent structure 100, 200 is intended to treat. That is, the stent structure 100, 200 is preferably selected/configured such that the stent structure 100, 200 contacts, but does not apply significant outward force against the inner surface of the stricture/lesion in an initial state. Because the stent structure 100, 200 initially only applies minimal force against the IEL of the stricture/lesion, the IEL is less likely to rupture or be otherwise damaged.

For example, for a stricture occluding 70% of a blood vessel, an appropriate number of stent cells 130, 230 would be covered by the restraining material 140, 240 to allow the stent structure 100, 200 to initially expand to 30% of the vessel diameter. Note that stent structures 100, 200 are typically specified such that the maximum/fully expanded diameter is greater than the unrestricted diameter of the body lumen the stent structure 100, 200 is intended to treat. Accordingly, in this example, if the stent structure 100, 200 is configured to expand to 30% of the diameter of the blood vessel, the stent structure 100, 200 will be configured have an initial expansion of less than 30% of its maximum/fully expanded diameter, for example and without limitation, 25%.

It is also preferable that the restraining material 140, 240 be applied to stent cells 130 in a uniform pattern such that when the stent structure 100, 200 is deployed in a body lumen, the stent structure 100, 200 expands in a uniform manner in the radial and longitudinal directions. Uniform radial and longitudinal expansion provides several advantages in both manufacture and operation of the stent structure 100, 200. For example, if the stent structure 100, 200 has uniform expansion characteristics, the stent structure 100, 200 may be loaded into a delivery system (e.g. delivery catheter, etc.) from either end without affecting performance. That is, in the preferred embodiment where both ends of the stent structure 100, 200 are functionally identical, the proximal end 340 and the distal end 350 of the stent are merely determined by the orientation of the stent structure 100, 200 in the delivery system (i.e. the end of the stent that is disposed closest to the proximal end of the delivery system is the proximal end 340 of the stent structure 100, 200 and the end closest to the distal end of the delivery system is the distal end 350 of the stent structure 100, 200). Thus, complex orientation control systems to ensure that stent structures 100, 200 are loaded into delivery systems from a particular end can be avoided.

Further, because the stent structure 100, 200 expands in a longitudinal and radially uniform manner, a physician does not have to select a stent structure 100, 200 that matches a particular longitudinal profile of a lesion/stricture; rather, the physician is able to specify a stent structure 100, 200 by simply selecting a stent having an initial expansion diameter, which is a function of the number of stent cells 130 restrained by the restraining material 140, 240, that is just smaller than, or preferably equal to the narrowest portion of the lesion/stricture. Moreover, the uniform initial expansion characteristics of the stent structure 100, 200 offer advantages in placement of the stent as the physician need only place the stent structure 100, 200 according the axial position of the lesion in the body lumen and without regard for the particular profile of the lesion. However, it should be understood that the restraining material 140, 240 may be applied to the stent structure 100, 200 in a non-uniform pattern, particularly in stents exceeding thirty (30) millimeters in length.

Figure 11:
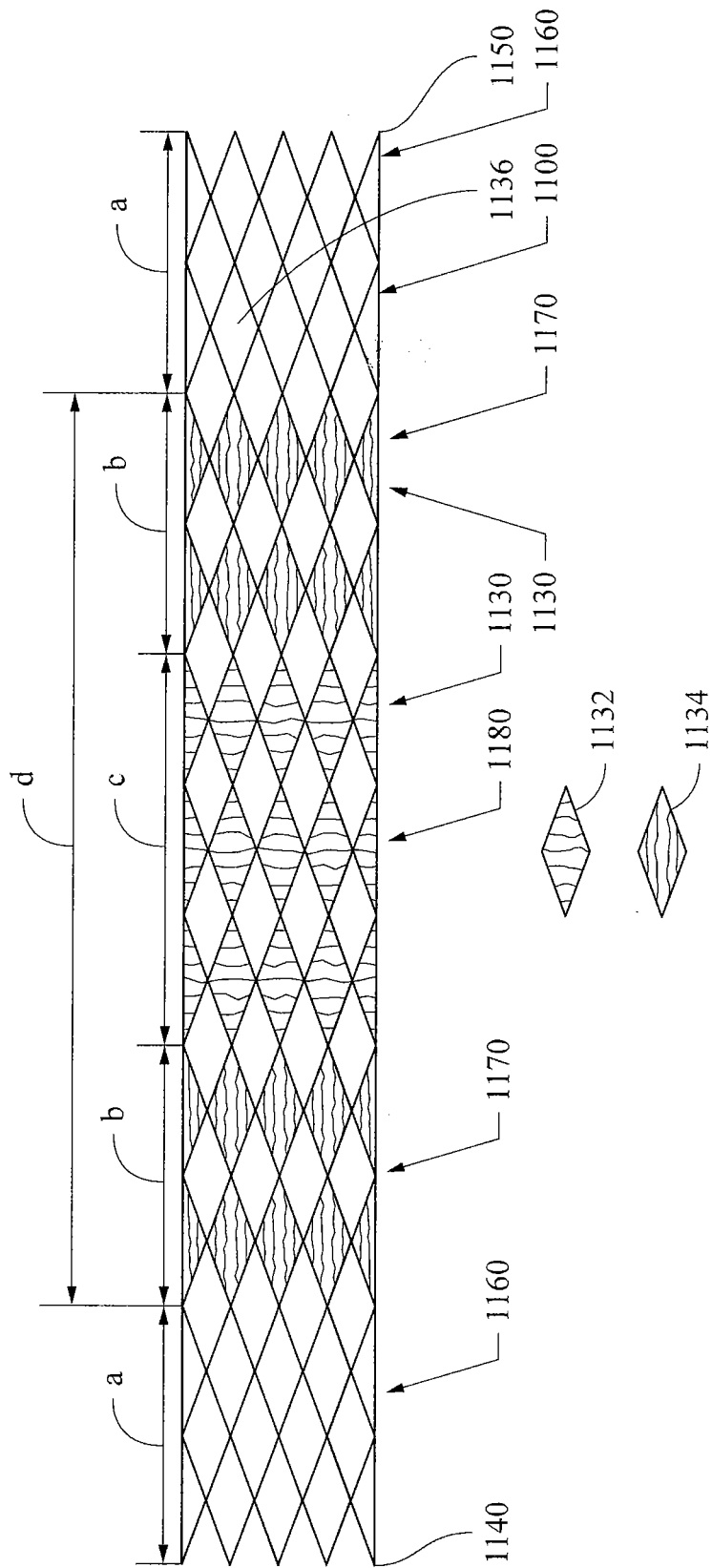
FIG. 11 is a side view of another embodiment of a gradually self-expanding stent.

The restraining material 140, 240 of different stent cells 130, 230 may be configured to degrade or stretch at different rates and times, depending on the thickness or chemical/physical makeup of the material. That is, the restraining material 140, 240 covering the area of some stent cells 130, 230 may be configured to degrade/stretch at a faster or slower rate as compared to the restraining material 140, 240 covering other stent cells 130, 230. As shown in FIG. 11, a stent structure 1100, which includes a plurality of open and unrestrained cells 1136 and a plurality of restrained stent cells, may be divided into three types of expansion regions: end regions 1160, intermediate regions 1170, and a central region 1180. The end regions 1160 correspond to the proximal and distal portions of the stent structure 1100. The end regions 1160 preferably extend inward a distance (a) toward the center of the stent structure 1100 from the proximal and distal ends 1140, 1150, respectively. For example, the distance (a) may be less than or equal to five (5) millimeters for stents having a length of thirty (30) millimeters or less, or ten (10) millimeters or less for stents having a length of (30) millimeters or more. The stent cells 1130 in the end regions 1160 are preferably open and unrestrained by a restraining material, such that they are free to immediately expand to their uncompressed diameter when released.

The intermediate regions 1170 extend toward the longitudinal center of the stent structure 110 by a length (b) from the distal end of the proximal end portion 1160 and the proximal end of the distal end portion 1160. Preferably, the length (b) is between 10-30% of the total length (d) between the proximal end of the distal end region 1160 and the distal end of the proximal end region 1160. For example, for a stent having a length (d) of eighty (80) millimeters, the length (b) may be between eight (8) and twenty-four (24) millimeters in length.

The stent cells 1130 in the intermediate region 1170 are covered by a restraining material 1134 having a first degradation/stretching rate. For example, the restraining material 1134 may be configured to degrade/stretch such that the stent cells 1130 in the intermediate region 1170 are completely released and free to assume the expanded configuration in, for example, 1-4 weeks, and preferably between 3-4 weeks.

The central region 1180 corresponds to a region centered in the longitudinal center of the stent structure 1100 and has a length (c) that extends between, and abuts the intermediate regions 1170. Preferably, the length (c) is between 40 to 80% of the total length (d) between the proximal end of the distal end region 1160 and the distal end of the proximal end region 1160.

The stent cells 1130 in the central region 1180 are covered by a restraining material 1132 having a second degradation rate that is slower than the first degradation rate of the restraining material 1134 of the intermediate portion 1170. Preferably, the second degradation rate is a whole integer multiple of the first degradation rate, e.g. 2×, 3×, etc. For example, if the restraining material 1134 is configured to degrade/stretch in 3 weeks, the restraining material 1132 may be configured to degrade/stretch in 6 weeks, or twice the amount of time the restraining material 1134 takes to degrade/stretch. Thus, over time, due to their faster degradation/stretching rate, the intermediate portions 1170 provide a smooth transition portion between the unrestricted end portions 1160 and the slower degrading/stretching central portion 1180. This configuration results in an hourglass type shape that allows the stent structure 1100 to gradually exert outward radial force against an inner surface of the lesion/stricture, which helps to reduce trauma to the IEL. Note that the restraining material 1132 may be made of a different material that has a greater resistance (and therefore a slower degradation/stretching rate) to degrading/stretching than the restraining material 1134. Alternatively, the slower degradation/stretching rate of the restraining material 1132 may be achieved by applying a thicker coating of the restraining material 1134 (e.g. twice the thickness, etc.).

It should be understood that while the embodiment of FIG. 11 has been described as having only intermediate and central restrained regions 1170 and 1180, the present invention is not limited thereto, and the stent structure 1100 may have a plurality of intermediate restrained regions having different degradation or stretching characteristics to achieve a smoother radial force gradient. Preferably, the degradation/stretching rates of the intermediate regions increase from both ends of the stent structure 1100 in a direction toward the stent structure's 1100 longitudinal center. It is also preferable that the degradation/stretching rate for each region, including the central region 1180, increases by a multiple of the outermost intermediate region 1170. For example, in a stent structure 1100 having two intermediate regions disposed on either side of the longitudinal center of the stent structure 1100, if the outermost intermediate region (first intermediate region) is configured to degrade in one week, the second intermediate regions, which are disposed adjacent to the first intermediate regions in an inboard direction, are configured to degrade in two weeks, while the central region 1180 is configured to degrade/stretch in 3 weeks, etc.

The degradation/stretching rate of the restraining material 140, 240 is based in large part on the properties of the material itself, as well as the thickness of the restraining material 140, 240. In some embodiments, the restraining material 140, 240 may comprise multiple layers of varying biodegradable polymers, each layer having a differing degradation rates. Some layers may utilize materials that biodegrade quickly while other layers may undergo prolonged degradation. In other embodiments, the restraining material 140, 240 may comprise a single layer of a biodegradable polymer or a composite layer made up of a combination of varying biodegradable polymers. In these embodiments, the single layer may degrade at a substantially uniform rate. In other embodiments, the restraining material 140, 240 may comprise a stretchable nonbiodegradable base material that is coated with one or more layers of biodegradable polymers in varying combinations and degradation rates. In these embodiments, within a given time period after the stent is deployed in a body lumen (preferably within 7 to 180 days), the one or more layers of biodegradable polymers will biodegrade, leaving only the nonbiodegradable base material. In other embodiments, the restraining material 140, 240 may comprise a single or multiple layers of stretchable material, and each layer may be configured to stretch at the same or different rates.

In any of these embodiments, one or more drugs may be incorporated into one or more layers of the restraining material 140, 240, such as anti-restenosis drugs, anti-inflammatory drugs, anti-thrombotic drugs, and growth factor or growth modulating drugs thereby inhibiting or accelerating tissue formation. These drugs may be mixed directly into one or more layers of the restraining material 140, 240 or may be enclosed within a pocket or opening in the restraining material itself for dispersion after biodegradation begins.

Additionally, the restraining material may be purposely dissolved at different points in time by applying an outside stimulus. For example ultrasonic heating or oral/systemic administration of an enzyme that is targeted to break down a particular restraining material 140, 240.

While the preceding description of embodiments of the present invention have been made with regard to self-expanding stents having specific geometrical structures, it should be understood that the present invention is not limited thereto, and the restraining material 140, 240 may be applied to any self-expanding stent having stent cells 130, 230 at least partially defined by circumferentially adjacent structural members of any geometry.

The gradually self-expanding stent may be manufactured by compressing the stent structure 100, 200 and inserting it into a cannula or other rigid structure. However, it should be understood that the rigid structure is not limited thereto, and may have any shape capable of restraining substantially the entirety of the stent in a compressed configuration. The cannula or other rigid structure preferably includes apertures that correspond to stent cells 130, 230 of the stent structure 100, 200. The apertures may have any number of shapes, including for example and without limitation, horizontally extending bars, circles, parallelograms, ovals, and the like. Further, the apertures may be approximately the same size and shape as the stent cells 130 in the compressed configuration, or the apertures may be larger than the area of the stent cells 130, 230. However, it is preferable that the apertures not be smaller than the area of the stent cells 130, 230 so that substantially the entirety of the area of the stent cell 130, 230 corresponding to the aperture can be covered by the restraining material 140, 240. Alternatively, the rigid structure may have a substantially open form, and the portions of the stent structure 100, 200 which the restraining material 140, 240 is not to be applied to may be masked off using adhesive tape, statically charged polymers, or the like.

Once the stent is housed within the rigid structure in its compressed configuration, the restraining material is applied to the outer surface of the stent structure 100, 200 through the apertures in the cannula. The restraining material may also be applied directly to the outside of the stent structure 100, 200 in the case of a masked stent. The restraining material may be applied by painting, spraying, pouring, or electro-spinning of particles, fibers, fluids or the like.

In embodiments constructed of super-elastic, shape-memory materials, such as nitinol, the stent structure may be cooled below its austenite temperature to facilitate compression.

Once the initial layer of restraining material 140, 240 is applied, subsequent layers of restraining material 140, 240 may be applied. These subsequent layers may be of the same or a different material. Further, the stent structure 100, 200 may be removed from the initial rigid structure and inserted into another rigid structure having apertures corresponding to different cells than the initial rigid structure, or corresponding to some of the apertures of the initial rigid structure. In this way, the restraining material 140, 240 covering different stent cells 130, 230 can be made thicker in some cells than others and/or made of multiple layers of different materials. Alternatively, subsequent and successive layers of material may be applied to select stent cells 130, 230 by masking off apertures of the initial rigid structure between coatings.

FIGS. 5-7 and 8-10 illustrate the operation of the gradually self-expanding stent shown in FIG. 4. FIG. 4 illustrates a gradually self-expanding stent structure 400 in a compressed form prior to deployment in a body lumen. The stent structure 400 includes of a plurality of interconnected structural members 410 that define a plurality of stent cells 430. Each stent cell 430 has an area that is defined by the circumferentially adjacent structural members 420. A restraining material 440 is attached to the circumferentially adjacent structural members 420 of a plurality of stent cells 430 such that the restraining material 440 substantially covers the entirety of the area of the stent cell, thereby connecting each of the structural members 420 and restraining the stent cell 430 in a compressed configuration. The restrained stent cells 430 are disposed in a pattern on the stent structure 400 such that the restraining material 440 does not extend around the circumference of the stent structure 400 so as to form a continuous circumferential band of restraining material 440. Additionally, the majority of the stent cells 430 to which the restraining material 440 is attached are located in a longitudinally central portion of the stent structure 400. The restraining material 440 is not attached to any of the stent cells 430 disposed at either end of the stent structure 440.

Initially, the stent structure 400 is inserted in a low-profile compressed configuration into the end of a delivery catheter. Typically, the delivery catheter includes a restraining sheath, and an inner catheter that includes a stop extending radially outward from a guide wire lumen of the inner catheter. A distal surface of the stop is disposed adjacent a proximal end of the stent structure 400.

In operation, initially, a guide-wire is advanced through a trocar into a desired vessel or cavity using the Seldinger technique, which is conventional and well known in the art. The guide-wire is then advanced through the patient's vasculature or cavity until it reaches the desired treatment site, for example a lesion/stricture 20 on a vessel wall 10. Once the guide-wire is in the desired position, the delivery catheter is then inserted into a patient's vasculature over the guide-wire, and advanced to the lesion/stricture 20 by sliding the delivery system along the guide-wire in a distal direction.

The stent structure 400 may be positioned at the lesion/stricture 20 using radiopaque markers located on the stent structure 400. The radiopaque markers allow a physician to visualize the stent structure 400 from outside the patient's body using x-ray fluoroscopy.

Once the stent is in position at the lesion/stricture 20, the physician retracts the retention sheath in the proximal direction using a control handle or the like. As the retention sheath is drawn in the proximal direction relative to the inner catheter, the stent structure 400 is pushed out of the retention sheath by the stop.

Figure 5:
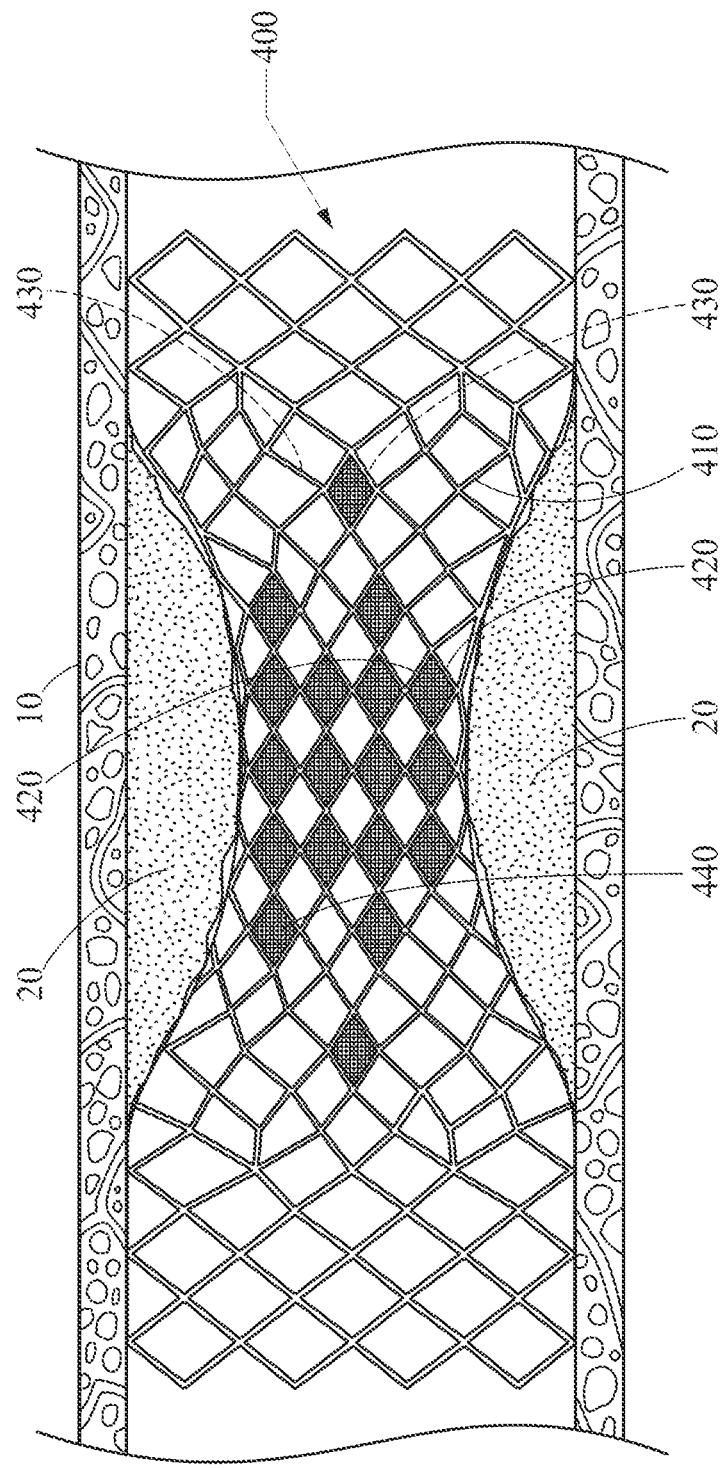
FIG. 5 is a side view of the self-expanding stent of FIG. 4 including biodegradable restraining material in an initial expansion stage after deployment within a body lumen.
Figure 6:
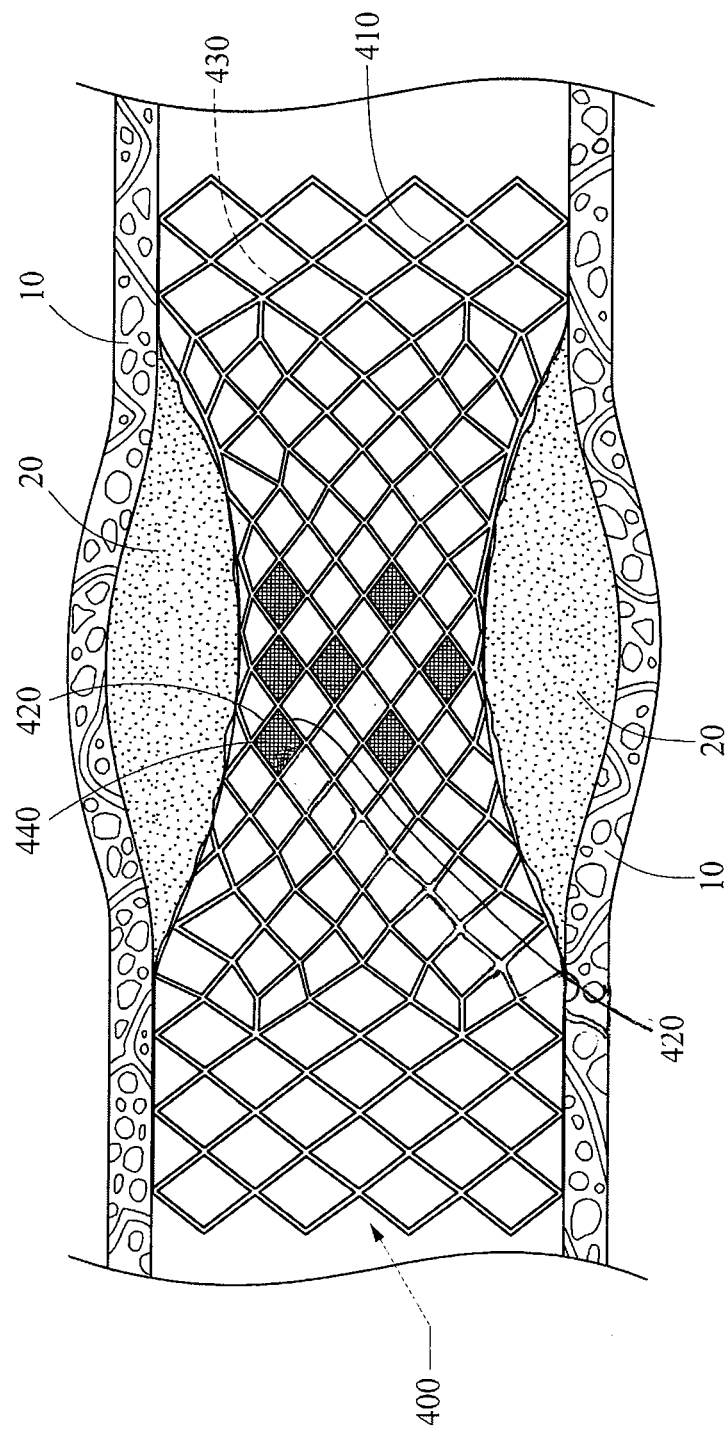
FIG. 6 is a side view of the self-expanding stent of FIG. 5 in an intermediate expansion stage after deployment.
Figure 7:
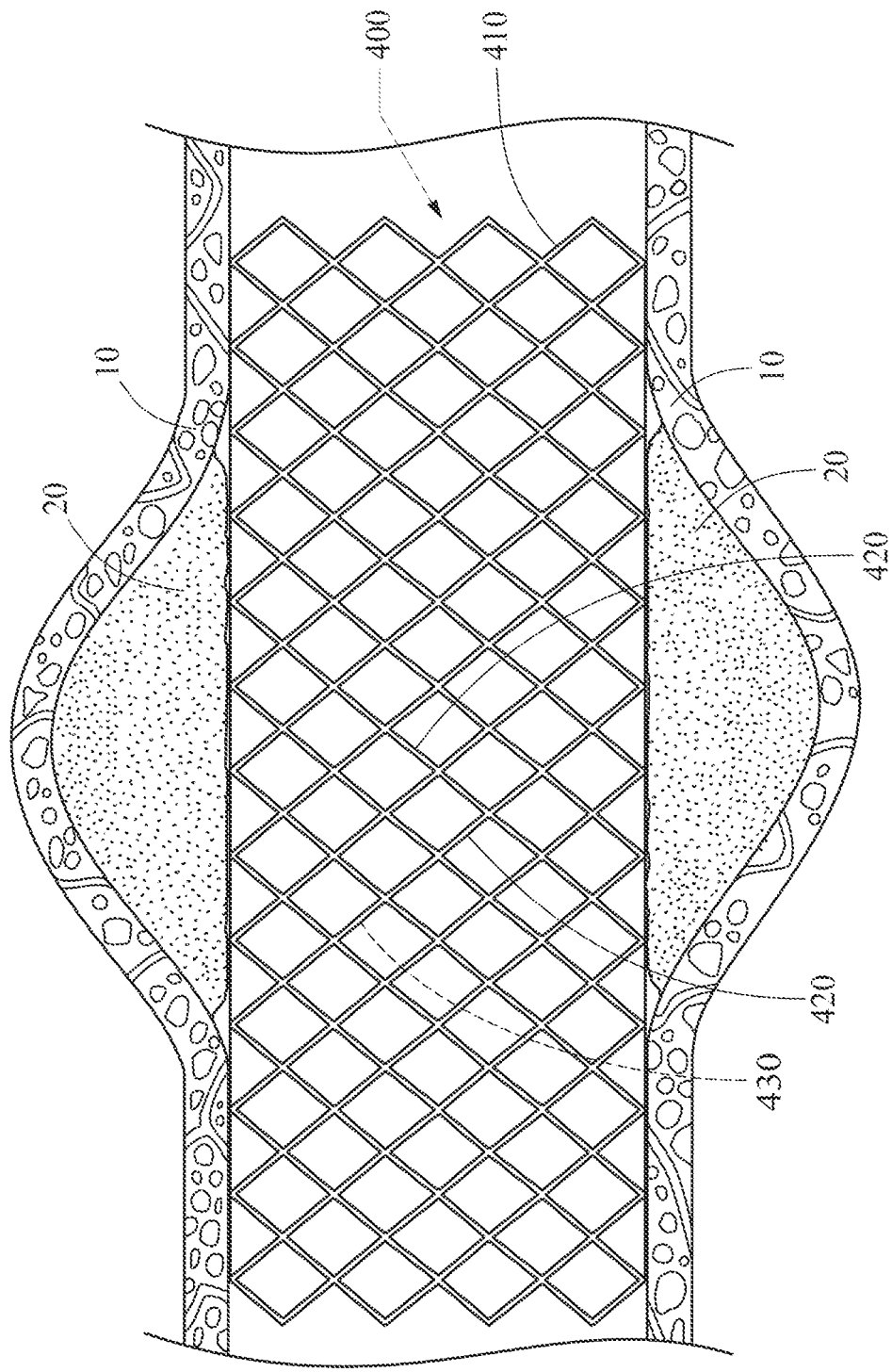
FIG. 7 is a side view of the self-expanding stent of FIG. 5 in a final expansion stage after deployment.

FIGS. 5-7 illustrate the operation of an embodiment of the stent structure 400 utilizing rigid, biodegradable restraining material 440. As shown in FIG. 5, once the stent structure 400 is released from the retention sheath, the proximal and distal ends of the stent structure 400, which do not have stent cells 430 restrained by restraining material 440, immediately expand in a radially outward direction and appose the wall of the blood vessel 10. Preferably, the stent structure is positioned such that the proximal and distal ends of the stent structure 400 contact healthy tissue when expanded. In addition to the stent cells 430 disposed at the proximal and distal ends of the stent structure 400, upon deployment, each of the stent cells 430 that is not covered by, or attached to, the restraining material 440 immediately expands to the maximum degree allowable. In contrast, each of the stent cells 430 that is covered by, and attached to the restraining material 440 generally maintains the same compressed, low-profile configuration as it had prior to deployment. Thus, the portions of the stent structure 400 containing restrained stent cells 430 are unable to fully expand, and assume a partially expanded configuration. The degree to which each portion of the stent structure 400 expands is directly related to the number of stent cells 430 that are covered by restraining material 440. Thus, the more stent cells 430 that are covered by restraining material 440 in a given area of the stent structure 400, the more compressed that area of the stent structure 400 remains. Preferably, the restrained stent cells correspond to the location and geometry of the lesion/stricture 20, thus preventing the stent structure 400 from exerting radial force against the lesion/stricture 20 and minimizing the potential for rupturing or damaging the IEL. Because the majority of the restrained stent cells are disposed in a longitudinally central portion of the stent structure 400, the stent structure 400 initially assumes an hourglass-like shape with the ends of the stent structure apposing healthy tissues of the vessel wall 10 and the center of the stent structure contacts, but does not apply significant outward force against the inner surface of the stricture/lesion 20. Preferably, the stent structure 100, 200 is not restrained away from the narrowest portion of the stricture/lesion 20 to avoid gaps that may promote the formation of thrombi.

As shown in FIGS. 6-7, over time, and preferably between seven (7) and one-hundred-eighty (180) days the restraining material 440 begins to degrade and release the restrained stent cells 430. Once the restraining material 440 of a sufficient number of stent cells 430 has degraded, the stent structure 440 begins to exert force in a radially outward direction against the lesion/stricture 20, thereby slowly and gradually forcing the lesion/stricture 20 to expand outward and open the blood vessel. Eventually, after all of the restraining material 440 is dissolved and all of the stent cells 430 assume their expanded configuration, the stent structure 400 opens the lesion/stricture 20 to, or close to the diameter of the vessel adjacent to the lesion/stricture 20.

Figure 8:
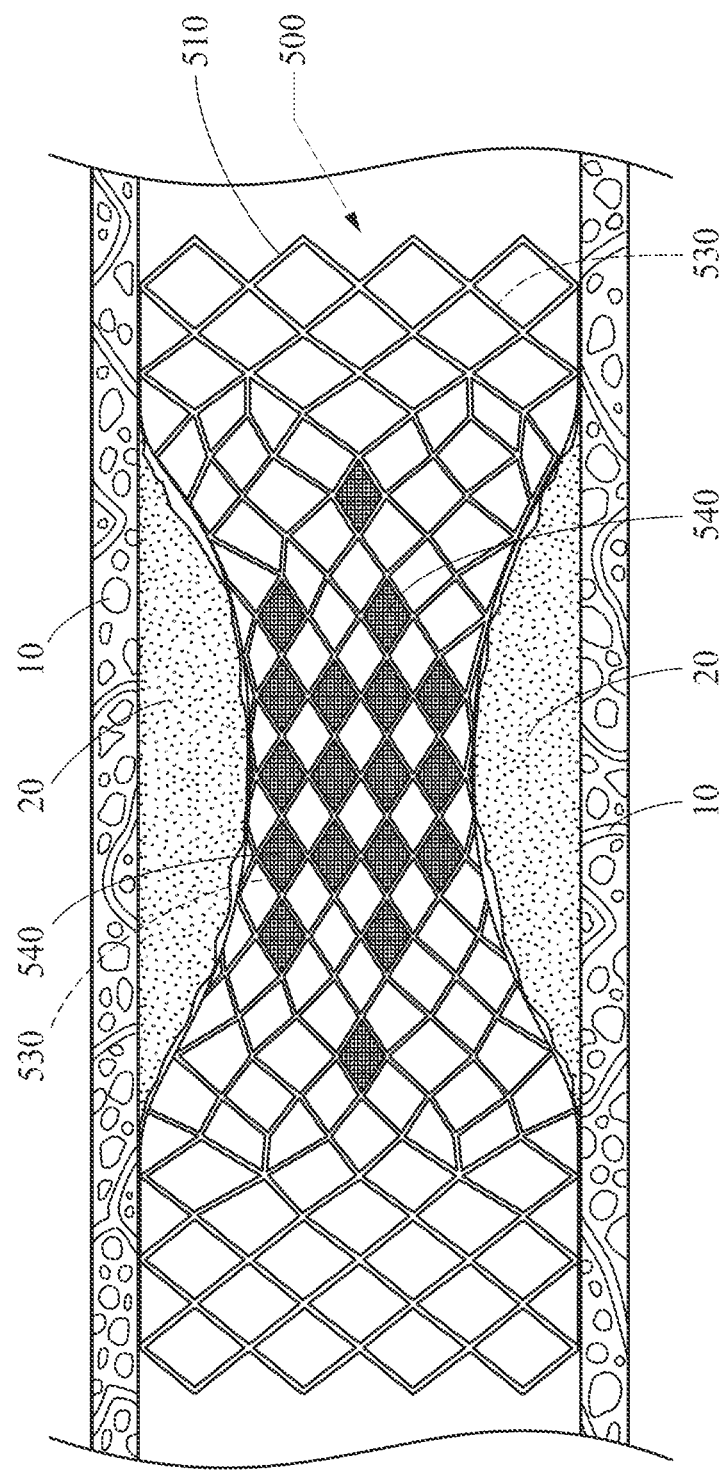
FIG. 8 is a side view of the self-expanding stent of FIG. 4 including a stretchable restraining material in an initial expansion stage after deployment within a body lumen.
Figure 9:
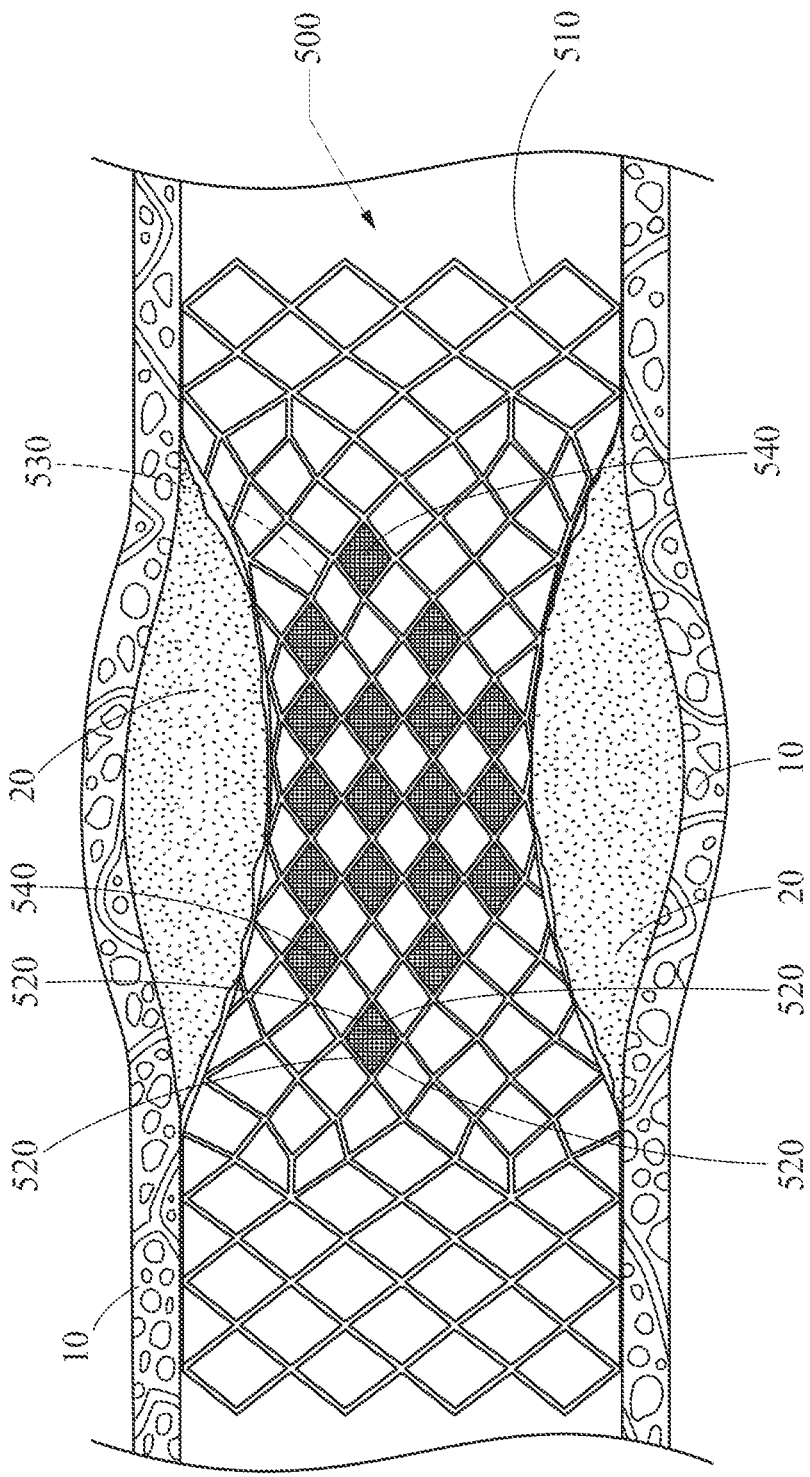
FIG. 9 is a side view of the self-expanding stent of FIG. 8 in an intermediate expansion stage after deployment.
Figure 10:
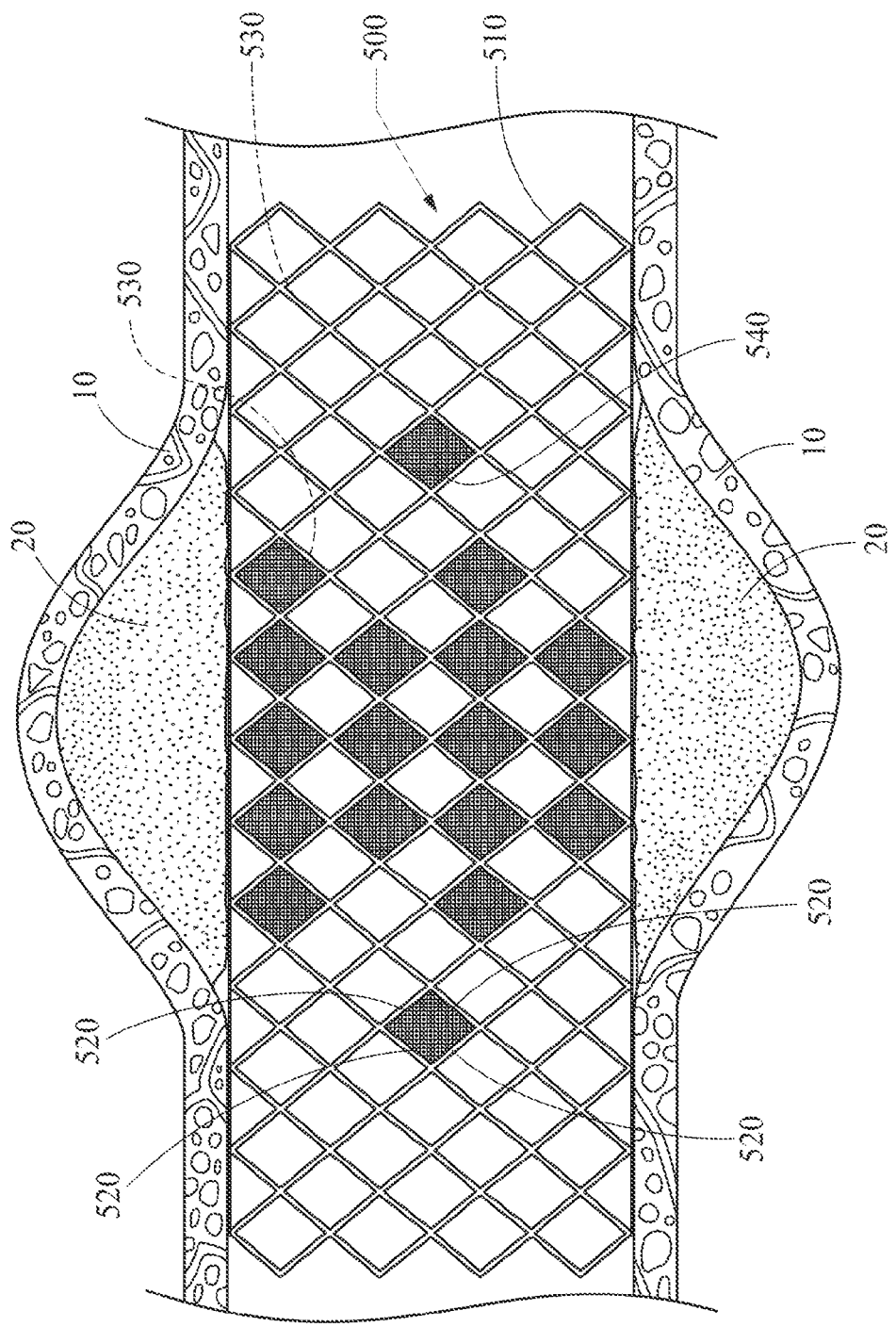
FIG. 10 is a side view of the self-expanding stent of FIG. 8 in a final expansion stage after deployment.

FIGS. 8-10 illustrate the operation of an embodiment of the stent structure 500 utilizing a stretchable restraining material 540. The stretchable restraining material 540 may be biodegradable, nonbiodegradable, or a combination thereof. As with the stent structure 400 utilizing rigid restraining material 440 described above, once the stent structure 500 is released from the retention sheath, the proximal and distal ends of the stent structure 500, which do not have stent cells 530 restrained by restraining material 540, immediately expand in a radially outward direction and appose the wall of the blood vessel 10. Preferably, the stent structure is positioned such that the proximal and distal ends of the stent structure 500 contact healthy tissue when expanded. In addition to the stent cells 530 disposed at the proximal and distal ends of the stent structure 500, upon deployment, each of the stent cells 530 that is not covered by, or attached to, the restraining material 540 immediately expands to the maximum degree allowable. In contrast, each of the stent cells 530 that is covered by, and attached to the restraining material 540, maintains the same compressed, low-profile configuration, or a slightly larger fixed initial profile as it had prior to deployment. Thus, the portions of the stent structure 500 containing restrained stent cells 530 are initially unable to expand against the vessel wall 10, and assume a partially expanded configuration. Preferably, the restrained stent cells correspond to the location and geometry of the lesion/stricture 20, thus preventing the stent structure 500 from exerting radial force against the lesion/stricture 20 and minimizing the potential for rupturing or damaging the IEL. Because the majority of the restrained stent cells are disposed in a longitudinally central portion of the stent structure 500, the stent structure 500 initially assumes an hourglass-like shape with the ends of the stent structure apposing healthy tissues of the vessel wall 10, and the center of the stent structure contacts, but does not apply significant outward force against the inner surface of the stricture/lesion 20.

As shown in FIGS. 8-10, over time, and preferably between seven (7) and one-hundred-eighty (180) days the restraining material 540 begins to stretch, thereby increasing the area of the restrained stent cells 530 and slowly allowing the stent structure 500 to expand. As the restraining material 540 continues to stretch, the stent structure 540 eventually begins to exert force against the lesion/stricture 20 in a radially outward direction. This outward pressure against the lesion/stricture slowly and gradually forces it to expand outward, thereby opening the blood vessel. Eventually, after the restraining material 540 is completely stretched out, the stent cells 530 assume their expanded configuration, and the stent structure 500 opens the lesion/stricture 20 to, or close to the diameter of the vessel adjacent to the lesion/stricture 20.

Accordingly, gradually self-expanding stents 400, 500 employing either rigid or stretchable restraining material, or a combination thereof, slowly apply radial force against the lesion/stricture 20, thereby allowing the IEL sufficient time to remodel and stretch without rupture or damage.

Figure 12:
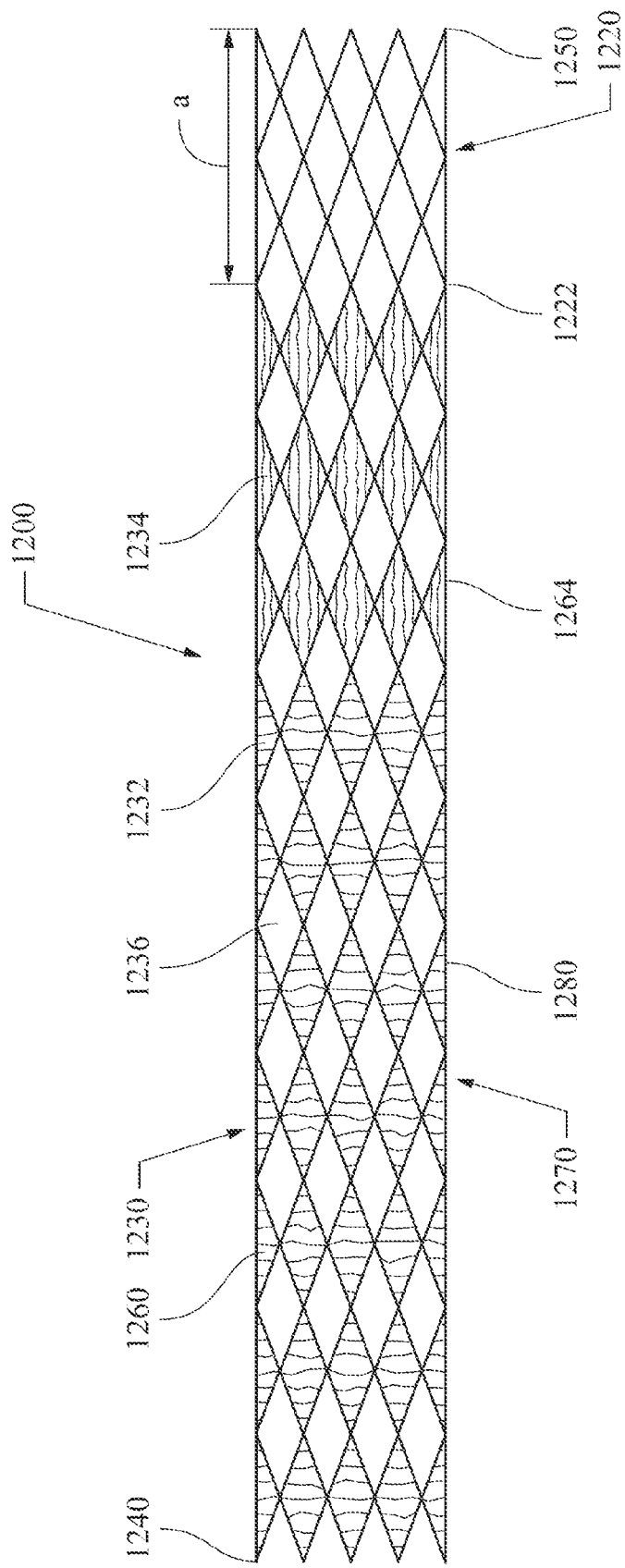
FIG. 12 is a side view of an another alternative embodiment of a gradually self-expanding stent.
Figure 13:
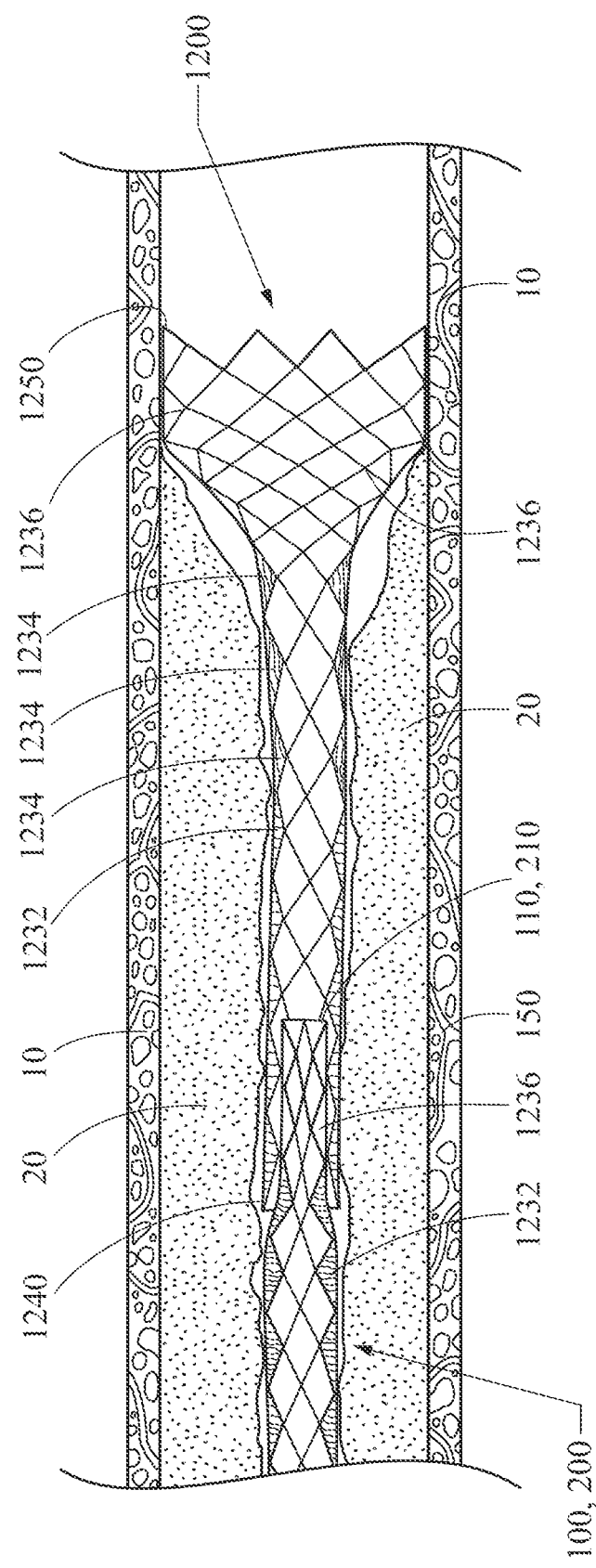
FIG. 13 is a partial side cross-sectional view of the gradually self-expanding stent of FIG. 12 in an initial expansion stage after deployment within a body lumen.

FIG. 12 illustrates an alternative embodiment of the gradually self-expanding stent 100, 200 that is designed to be used in conjunction with one or more gradually self-expanding stent structures 100, 200, or a conventional self-expanding stent, in an overlapping manner to treat very long lesions/strictures 20 (e.g. lesions/strictures exceeding a length of 100 mm), as shown in FIG. 13. The self-expanding stent 1200 may consist of two portions, a distal portion 1220, and a proximal portion 1230. The distal portion extends from the distal end 1250 toward the proximal end 1240 of the stent structure 1200 by a distance (a), which may be, for example, between 5 and 10 millimeters. The proximal portion 1230 extends from the proximal end of the distal portion 1222 to the proximal end of the stent structure 1240. The proximal portion 1230 includes a plurality of stent cells 1270. A restraining material 1260 is applied to the stent struts 1280 defining some of the stent cells 1270 (preferably 50%) in the proximal portion 1230 such that the restraining material 1260 covers the substantially the entire area of the stent cells 1270. In a preferred embodiment, the proximal portion 1230 may include some restrained stent cells 1234 disposed at a longitudinally distal portion covered in a restraining material 1264 that is configured to degrade or stretch more slowly than the restrained stent cells 1232 covered in a restraining material 1260, as described above in conjunction with FIG. 3. However, unlike the embodiment shown in FIG. 3, the restrained stent cells 1232 extend all the way to the proximal end 1240 of the stent structure 1200. Thus, when the stent structure 1200 is deployed in a body lumen, only the distal portion 1220 is free to immediately expand out and appose the inner wall of the body lumen, while the proximal end 1240 remains in the same partially expanded configuration as the proximal portion 1230.

As shown in FIG. 13, when the stent structure 1200 (the "primary stent") is deployed in a body lumen 10 having a long lesion/stricture 20, the distal portion of the stent structure 1200 expands out to, and apposes the inner diameter of the body lumen 10 such that the distal end 1250 of the stent structure 1200 is anchored to the healthy tissue of the body lumen 10 and will not migrate within the body lumen 10. Once the stent structure 1200 is deployed, a second self-expanding stent having a configuration similar to the stent structure 100, 200 (the secondary stent) described above with regard to FIGS. 1-3, is guided to the treatment site using the Seldinger technique such that the distal end 110, 210 of the stent structure 100, 200 is inserted into the proximal end 1240 of the stent structure 1200. The secondary stent 100, 200 is then advanced into the proximal end 1240 of the primary stent 1200 such that the distal portion of the secondary stent 100, 200, which consists of open and unrestrained stent cells 1236, is disposed inside the primary stent 1200. The secondary stent 100, 200 is then released and the unrestrained distal portion of the secondary stent 100, 200 immediately expands out to the inner diameter of the primary stent 1200, such that the outer surface of the stent struts in the distal portion of the secondary stent 100, 200 appose the inner surface of corresponding stent struts of the proximal portion of the primary stent 1200. Once deployed, the combination of the primary stent 1200 and the secondary stent 100, 200 results in a gradually self-expanding stent system having proximal and distal ends that appose healthy tissue of the body lumen 10 at either end of the lesion/stricture 20, and that remains partially compressed in the central portion corresponding to the lesion/stricture 20.

Note that the increased outward radial force exerted on the portion of the primary stent 1200 by the distal portion of the secondary stent 100, 200 preferably does not cause that portion of the primary stent 1200 to initially expand when the secondary stent 100, 200 is deployed. In an alternative embodiment, the restraining material 1260 covering the stent cells 1270 of the proximal portion 1230 that is likely to interface with the distal portion of the secondary stent 100, 200 may be modified to counteract the additional outward radial force exerted by the secondary stent 100, 200. For example, the restraining material 1260 in these areas may be thicker, or made of a stronger material.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A self-expanding stent, comprising:
    a stent structure comprising a plurality of stent cells having a compressed configuration and an expanded configuration, said stent structure being self-expanding from said compressed configuration to said expanded configuration;
    a first region and two second regions of said stent structure, said first region being disposed longitudinally between said second regions, said first region comprising a first plurality of said stent cells and a second plurality of said stent cells dispersed circumferentially amongst said first plurality of said stent cells, each of said first plurality of said stent cell comprising at least a pair of circumferentially adjacent structural members connected to each other through a first bend;
    a first restraining material attached to said first region of said stent structure and extending across an entirety of a first material area defined by the pair of circumferentially adjacent structural members and the first bend, said second plurality of said stent cells being unrestrained by the first restraining material, said first restraining material initially restraining said first region from expanding to said expanded configuration, and said first restraining material releasing said first region over time to allow said first region to expand to said expanded configuration; and
    wherein said second regions of said stent structure expand at a faster rate than said first region.

2. The self-expanding stent according to claim 1, wherein said second regions are open and unrestrained by any restraining material, said second regions thereby being free to immediately expand to said expanded configuration.

3. The self-expanding stent according to claim 1, wherein said second regions are disposed at a most proximal end and a most distal end of said stent structure.

4. The self-expanding stent according to claim 1, further comprising two third regions, said first region and said second regions being disposed longitudinally between said third regions, and a second restraining material attached to said second regions of said stent structure, said second restraining material initially restraining said second regions from expanding to said expanded configuration, and said second restraining material releasing said second regions over time to allow said second regions to expand to said expanded configuration, wherein said second restraining material releases said second regions at a faster rate than said first restraining material releases said first region.

5. The self-expanding stent according to claim 4, wherein said third regions are open and unrestrained by any restraining material, said third regions thereby being free to immediately expand to said expanded configuration.

6. The self-expanding stent according to claim 5, wherein said third regions are disposed at a most proximal end and a most distal end of said stent structure.

7. The self-expanding stent according to claim 1, wherein each of said first plurality of said stent cells in said first region comprising a second bend in addition to the first bend, said respective first and second bends facing each other and being longitudinally spaced apart, a plurality of structural members including the pair of circumferentially adjacent structural members and connecting said first and second bends, wherein each structural member has a length, each of said first plurality of said stent cells being defined by said first and second bends and said lengths of said plurality of structural members, and said first restraining material is attached to said first plurality of said stent cells along the entire length of said structural members, said first restraining material extending across an entirety of a second material area defined by said first and second bends and said plurality of structural members of each of said stent cells in said first plurality of said stent cells, said first restraining material thereby extending longitudinally across each of said second material areas between said first and second bends and circumferentially across each of said second material areas between said plurality of structural members disposed adjacent each other.

8. The self-expanding stent according to claim 7, wherein the second plurality of said stent cells is dispersed amongst said first plurality of said stent cells in a circumferentially uniform manner, said second plurality of said stent cells being open and unrestrained by any restraining material, said second plurality of said stent cells thereby being free to immediately expand.

9. The self-expanding stent according to claim 8, wherein a proportion of said first plurality of said stent cells to said second plurality of said stent cells is substantially equal.

10. The self-expanding stent according to claim 1, wherein said first region is disposed at a longitudinally central portion of said stent structure.

11. The self-expanding stent according to claim 10, wherein said first region is between 40% to 80% of a total length of said stent structure.

12. The self-expanding stent according to claim 1, wherein said first restraining material is biodegradable.

13. The self-expanding stent according to claim 1, wherein said first region is disposed at a longitudinally central portion of said stent structure, said first restraining material is biodegradable, said second regions are open and unrestrained by any restraining material, said second regions thereby being free to immediately expand to said expanded configuration, and said second regions are disposed at a most proximal end and a most distal end of said stent structure.

14. The self-expanding stent according to claim 13, wherein each of said first plurality of said stent cells in said first region comprising a second bend in addition to the first bend, said respective first and second bends facing each other and being longitudinally spaced apart, a plurality of structural members including the pair of circumferentially adjacent structural members and interconnecting said first and second bends, wherein each structural member has a length, each of said first plurality of said stent cells being defined by said first and second bends and said lengths of said plurality of structural members, and said first restraining material is attached to said first plurality of said stent cells along the entire length of said structural members, said first restraining material extending across an entirety of a second material area defined by said first and second bends and said plurality of structural members of each of said stent cells in said first plurality of said stent cells, said first restraining material thereby extending longitudinally across each of said second material areas between said first and second bends and circumferentially across each of said second material areas between said plurality of structural members disposed adjacent each other.

15. The self-expanding stent according to claim 14, wherein said second plurality of said stent cells is dispersed amongst said first plurality of said stent cells in a circumferentially uniform manner, said second plurality of said stent cells being open and unrestrained by any restraining material, said second plurality of said stent cells thereby being free to immediately expand.

16. The self-expanding stent according to claim 15, wherein said first region is between 40% to 80% of a total length of said stent structure.

17. The self-expanding stent according to claim 1, further comprising two third regions, said first region and said second regions being disposed longitudinally between said third regions, and a second restraining material attached to said second regions of said stent structure, said second restraining material initially restraining said second regions from expanding to said expanded configuration, and said second restraining material releasing said second regions over time to allow said second regions to expand to said expanded configuration, wherein said second restraining material releases said second regions at a faster rate than said first restraining material releases said first region, said first restraining material is biodegradable, said first region is disposed at a longitudinally central portion of said stent structure, and said third regions are disposed at a most proximal end and a most distal end of said stent structure.

18. The self-expanding stent according to claim 17, wherein said third regions are open and unrestrained by any restraining material, said third regions thereby being free to immediately expand to said expanded configuration.

19. The self-expanding stent according to claim 18, wherein each of said first plurality of said stent cells in said first region comprising a second bend in addition to the first bend, said respective first and second bends facing each other and being longitudinally spaced apart, a plurality of structural members including the pair of circumferentially adjacent structural members and interconnecting said first and second bends, wherein each structural member has a length, each of said first plurality of said stent cells being defined by said first and second bends and said lengths of said plurality of structural members, and said first restraining material is attached to said first plurality of said stent cells along the entire length of said structural members, said first restraining material extending across an entirety of a second material area defined by said first and second bends and said plurality of structural members of each of said stent cells in said first plurality of said stent cells, said first restraining material thereby extending longitudinally across each of said second material areas between said first and second bends and circumferentially across each of said second material areas between said plurality of structural members disposed adjacent each other, said second plurality of said stent cells dispersed amongst said first plurality of said stent cells in a circumferentially uniform manner, said second plurality of said stent cells being open and unrestrained by any restraining material, said second plurality of said stent cells thereby being free to immediately expand, and said second regions of said stent structure comprises a third plurality of said stent cells, each of said third plurality of said stent cells in said second regions comprising a third bend and a fourth bends, said respective third and fourth bends facing each other and being longitudinally spaced apart, said plurality of structural members interconnecting said third and fourth bends, each of said third plurality of said stent cells being defined by said third and fourth bends and said lengths of said plurality of structural members, and said second restraining material is attached to said third plurality of said stent cells along the entire length of said structural members, said second restraining material extending across an entirety of a third material area defined by said third and fourth bends and said plurality of structural members of each of said stent cells in said third plurality of said stent cells, said second restraining material thereby extending longitudinally across each of said third material areas between said third and fourth bends and circumferentially across each of said third material areas between said plurality of structural members disposed adjacent each other, and said second regions of said stent structure further comprises a fourth plurality of said stent cells dispersed amongst said third plurality of said stent cells in a circumferentially uniform manner, said fourth plurality of said stent cells being open and unrestrained by any restraining material, said fourth plurality of said stent cells thereby being free to immediately expand.

20. The self-expanding stent according to claim 19, wherein a proportion of said first plurality of said stent cells to said second plurality of said stent cells is substantially equal, a proportion of said third plurality of said stent cells to said fourth plurality of said stent cells is substantially equal, and said first region is between 40% to 80% of a total length of said stent structure.

21. A self-expanding stent, comprising:
  a stent structure having a circumference and comprising a plurality of stent cells having a compressed configuration and an expanded configuration, said stent structure being self-expanding from said compressed configuration to said expanded configuration;
  a first region and two second regions of said stent structure, said first region being disposed longitudinally between said second regions;
  a first restraining material attached to said first region of said stent structure and forming regions about the circumference, said regions being circumferentially discontinuous, said first restraining material initially restraining said first region from expanding to said expanded configuration, and said first restraining material releasing said first region over time to allow said first region to expand to said expanded configuration; and
  wherein said second regions of said stent structure expand at a faster rate than said first region.

\* \* \* \* \*